(12) United States Patent
Miller et al.

(10) Patent No.: US 7,052,472 B1
(45) Date of Patent: May 30, 2006

(54) SYSTEMS AND METHODS FOR DETECTING SYMPTOMS OF HYPOGLYCEMIA

(75) Inventors: Mark Edward Miller, Vancouver (CA); Ronald William Evans, Delta (CA)

(73) Assignee: DSP Diabetes Sentry Products, Inc., Maple Ridge (CA)

( * ) Notice: Subject to any disclaimer, the term of this patent is extended or adjusted under 35 U.S.C. 154(b) by 246 days.

(21) Appl. No.: 10/740,695

(22) Filed: Dec. 18, 2003

Related U.S. Application Data

(60) Provisional application No. 60/434,606, filed on Dec. 18, 2002.

(51) Int. Cl.
*A61B 5/05* (2006.01)

(52) U.S. Cl. ..................................... 600/549

(58) Field of Classification Search ................ 600/549, 600/547, 365; 374/142, 185
See application file for complete search history.

(56) References Cited

U.S. PATENT DOCUMENTS

| | | | | |
|---|---|---|---|---|
| 4,178,916 A | * | 12/1979 | McNamara | 600/547 |
| 4,365,637 A | * | 12/1982 | Johnson | 600/547 |
| 4,509,531 A | * | 4/1985 | Ward | 600/549 |
| 5,559,497 A | | 9/1996 | Hong | |
| 5,844,862 A | | 12/1998 | Cocatre-Zilgien | |
| 5,897,505 A | | 4/1999 | Feinberg et al. | |
| 5,938,593 A | | 8/1999 | Ouellette | |
| 2002/0106709 A1 | * | 8/2002 | Potts et al. | 435/14 |
| 2005/0101875 A1 | * | 5/2005 | Semler et al. | 600/509 |

OTHER PUBLICATIONS

Hansen et al., "Teledyne Sleep Sentry: Evaluation in pediatric patients for detection of nocturnal hypoglycemia", Diabetes Care, Nov.-Dec. 1983, pp. 597-600, vol. 6, No. 6.
Clarke et al., "Metabolic and cutaneous events associated with hypoglycemia detected by Sleep Sentry", Diabetes Care, Sep. 1988, pp. 630-635, vol. 11, No. 8.
Trecroci, D., "Too rich for my blood glucose", Diabetes Interview, Jul. 2002, pp. 28-30, vol. 11, No. 7.

(Continued)

*Primary Examiner*—Robert L Nasser
(74) *Attorney, Agent, or Firm*—Michael R. Schacht; Schacht Law Office, Inc.

(57) ABSTRACT

A system for detecting symptoms of hypoglycemia in a diabetic individual. The system comprises a temperature sensing system, a conductance sensing system, a trending system, a threshold system, and an alarm system. The temperature sensing system produces a temperature signal representative of a skin temperature of the diabetic individual. The conductance sensing system produces a conductance signal representative of a level of perspiration of the diabetic individual. The trending system produces a slope estimate representative of a rate of change of the skin temperature over a predetermined interval in response to the temperature signal. The threshold system produces a slope threshold representative of a hypoglycemic decline in skin temperature observed over the predetermined interval in response to the conductance signal and to the temperature signal. The alarm system produces an indication of the presence of hypoglycemic symptoms in response to the slope estimate and the slope threshold.

27 Claims, 4 Drawing Sheets

OTHER PUBLICATIONS

D'Souza, S., "TB004: Automatic calibration of the WDT time-out period", 1996, Microchip Technology Inc., Chandler AZ.

Cox, D., "AN512: Implementing ohmmeter/temperature sensor", 1997, Microchip Technology Inc., Chandler AZ.

Palacherla, A., "AN510: Implementation of a asynchronous serial I/O", 1997, Microchip Technology Inc., Chandler AZ.

Cygnus Inc., "Summary of safety and effectiveness data (Automatic Glucose Biographer)", P990026, Mar. 22, 2001, US FDA CDRH (www.fda.gov/cdrh/pdf/p990026.html).

Cygnus Inc., "Summary of safety and effectiveness data (Automatic Glucose Biographer)", P990026/S008, Aug. 26, 2002, US FDA CDRH (www.fda.gov/cdrh/pdf/p990026s008.html).

* cited by examiner

SYSTEMS AND METHODS FOR DETECTING SYMPTOMS OF HYPOGLYCEMIA

RELATED APPLICATIONS

This application claims priority of U.S. Provisional Patent Application Ser. No. 60/434,606, filed on Dec. 18, 2002.

FIELD OF THE INVENTION

The present invention generally relates to the field of physiological measurement and, more particularly, to apparatus for monitoring surface temperature and conductivity of the skin as a means of detecting symptoms associated with hypoglycemia in a diabetic individual.

BACKGROUND OF THE INVENTION

Hypoglycemia, in lay terms known as "low blood sugar" or "insulin shock", is an undesirable and potentially lethal side-effect of insulin treatment in diabetes mellitus. Hypoglycemia triggers a hypothalamic stress response, resulting in increased activity in the sympathetic nervous system and release of the catecholamine hormones epinephrine and norepinephrine from the adrenal medulla. Catecholamine release into the blood stream induces excitatory or adrenergic responses such as shakiness, increased heart rate and perspiration, and cutaneous vasoconstriction, potentially resulting in paleness and a drop in skin temperature. Over a period of hours, declining blood glucose concentration may ultimately affect the brain and lead to neuroglycopenic symptoms such as dizziness, impaired coordination, mental confusion, and altered behaviour. If left untreated, extreme hypoglycemia may result in coma, brain damage or death.

Upon becoming aware of early autonomic indicators like increased perspiration or heart palpitations, a diabetic individual can easily correct mild hypoglycemia by taking fast-acting carbohydrate, such as glucose tablets, fruit juice, or candies. However, cognizance of adrenergic symptoms may be compromised by diabetic autonomic neuropathy, a nervous disorder that is likely attributable to a combination of factors including high blood glucose and a long duration of diabetes.

Cognizance of physical symptoms is also reduced or inhibited by "hypoglycemia unawareness", an increased tolerance to low blood sugar which develops as a result of repeated hypoglycemic episodes. Since epinephrine response is blunted during sleep and as a consequence of hypoglycemia unawareness caused by neuropathy or frequent lows, a sleeping diabetic individual may not awaken until after nueroglycopenic symptoms are established, in which case the individual in a confused mental state may neglect or even resist treatment. Therefore, it is particularly important to provide methods of preventing nocturnal hypoglycemic events at the earliest possible stage of detection, so that development of hypoglycemia unawareness is avoided.

One approach which may be applied to detection of nocturnal hypoglycemia is described by Potts and Tierney in U.S. Patent Application Publication 2002/0106709. Potts and Tierney disclose methods and devices for prediction of hypoglycemic events based on analysis of discrete sampled values of glucose, body temperature, and skin conductance. Skin conductance is directly representative of the adrenergic symptom of perspiration. In the preferred embodiment, glucose is measured by a GlucoWatch G2 Biographer (Cyngnus Inc. Redwood City Calif.), rather than by blood sampling.

The GlucoWatch is applied at the wrist and withdraws glucose in the subcutaneous interstitial fluid into a hydrogel pad by means of reverse-iontophoresis, a process in which an osmotic flow through the epidermis is driven by a current applied at the skin surface. Hypoglycemic detection thresholds for interstitial glucose, skin temperature, and skin conductance measurements are derived for a given individual from historical data collected over extended time periods (days, weeks or months). Methods are proposed by Potts and Tierney for predicting a future glucose value at time (n+1) from extrapolation of past glucose values up to and including time (n). A hypoglycemic event is predicted when comparison of the extrapolated interstitial glucose to the glucose threshold indicates a hypoglycemic event, provided that comparison of either skin temperature or conductance, or both, to their respective thresholds also indicates a hypoglycemic event.

In principle, therefore, methods disclosed by Potts and Tierney rely on the presence of adrenergic symptoms to validate an interstitial glucose reading suggestive of a low blood glucose concentration. However, as the glucose reading derived by the GlucoWatch is not obtained from the blood, the manufacturer of the instrument directs users to confirm readings by glucometer under certain circumstances, such as during a hypoglycemic episode.

A central limitation of methods described by Potts and Tierney is the uncertainty of the subcutaneous glucose reading as electro-osmotically obtained from the interstitial fluid. Clinical performance of the GlucoWatch Biographer has been reviewed by the US Food and Drug Administration as documented in "Summary of Safety and Effectiveness Data" (SSED), PMA no. P990026 (Mar. 22, 2001), and as documented in the SSED for PMA supplement P990026/1008 (Aug. 26, 2002). As reported in these FDA SSED publications, individual GlucoWatch readings can differ substantially from concurrently recorded blood glucose values, such individual differences being somewhat unpredictable and necessitating interpretation based on trends and patterns seen with several sequential readings over time.

The GlucoWatch requires 20 minutes to produce each glucose reading, and as such, dynamic response of the interstitial glucose measurement may substantially lag blood glucose variations. Prediction of the glucose value as disclosed by Potts and Tierney is therefore an attempt to overcome the slow response of the GlucoWatch to changes in interstitial glucose concentration. However, extrapolation of an upcoming value 20 minutes in advance based on uncertain prior values may invalidate the hypoglycemic threshold comparison, and so methods as disclosed by Potts and Tierney require additional temperature and skin conductivity analyses to either support or reject the comparison result.

As a means of reducing noise in the glucose values and thereby obtaining improved prediction, Potts and Tierney disclose a linear prediction equation based on moving average exponential smoothing over a 60-minute interval, however, the equation utilizes only the current glucose reading and previous two readings to extrapolate the prediction result. Therefore, the protracted sample processing time of the GlucoWatch also limits the amount of data that may be meaningfully applied to obtain useful predictions of the interstitial glucose.

Further practical limitations of the GlucoWatch include a three-hour warm-up interval following application to the wrist, which must be completed prior to initiation of monitoring. Once monitoring has been initiated, rapid temperature change or excessive perspiration can cause the GlucoWatch to discard glucose measurements, and if such conditions persist, the GlucoWatch will cease monitoring altogether.

Skin irritation and/or itching from iontophoresis is experienced by most users, and as such the GlucoWatch must be relocated to a new site on the arm, or to the alternate arm, prior to each use. Occasional blisters may be observed, and people with sensitive skin may experience more intense, although temporary, redness and itching. In consideration of skin irritations induced, the GlucoWatch must not be applied at sites having eczema, cuts, sunburn, razor burn or scarring, and to be effective the GlucoWatch cannot be applied over hair.

Given that induced skin irritation may be tolerable for some users, and that inconvenience of a protracted warm-up delay prior to use may be acceptable, and that removal of hair from the upper limbs is not objectionable, the 12-hour replacement cycle of the disposable hydrogel pad creates a significant economic burden for those desiring or requiring frequent glucose readings on a ongoing basis (Trecroci, D., Diabetes Interview, 11:28–30 (2002)). Due to performance limitations, side-effects, and unmanageable operating costs, the GlucoWatch may not become widely utilized, particularly for those individuals requiring nocturnal monitoring for hypoglycemic episodes over a lifetime.

Alternate approaches to the problem of detecting nocturnal hypoglycemia predate development of the GlucoWatch Biographer. Such methods rely solely on automated monitoring for early-stage adrenergic symptoms, such as perspiration and skin temperature drop, as opposed to direct measurement of blood, skin or interstitial glucose concentration. Detection of pertinent symptoms causes an audible alarm to be produced, awakening the user who must then confirm the condition by blood sample, this also being the case for the GlucoWatch as described above. An advantage of a symptom-based approach is that it may be implemented as a small, relatively inexpensive electronic monitor that may be conveniently worn, like the GlucoWatch, at the wrist or other sites. Additional advantages include low operating cost, because the alternate approaches do not employ a disposable component, and no skin irritation, because the alternates to the GlucoWatch do not employ reverse-iontophoresis when determining either skin temperature or perspiration.

However, acceptance of simple electronic monitors has been limited by their inability to reliably distinguish symptoms of hypoglycemia from ongoing physiological variations not associated with hypoglycemia, or from transient environmental disturbances. Annoying false alarms may thus be produced as a result of, for example, increased perspiration or reduced skin blood flow arising from the normal autonomic function of the hypothalamus in maintaining core body temperature. Similarly, false alarms may also result in response to the physiological effects of medication or infection insofar as these influence the thermoregulatory mechanism, or other responses of the autonomic nervous system. Transient disturbances not associated with any autonomic process, for example air drafts and body movement, may also result in false alarms if means are not provided to mitigate such noise sources.

Monitors that combine measurement of a temperature with measurement of skin moisture or perspiration are disclosed by Ouellete in U.S. Pat. No. 5,938,593, and by Fienberg et al. in U.S. Pat. No. 5,897,505. Additionally, apparatus which measure skin temperature and produce an alarm signal when the temperature either rises above or falls below a threshold are also disclosed by Hong in U.S. Pat. No. 5,559,497, and by Cocatre-Zilgien in U.S. Pat. No. 5,844,862. Monitors intended for detecting hypoglycemic symptoms in a diabetic individual, combining measurement of perspiration, temperature or both with means for producing an alarm are also disclosed in U.S. Pat. No. 4,178,916 to McNamara, U.S. Pat. No. 4,365,637 to Johnson, and U.S. Pat. No. 4,509,531 to Ward.

U.S. Pat. No. 4,178,916 to McNamara describes a diabetic insulin alarm system that is applied to the wrist and which produces an alarm if the temperature measured at the skin surface drops below a threshold. McNamara also describes means which produce an alarm if perspiration at the wrist increases such that the galvanic skin resistance between two electrodes correspondingly decreases below a threshold. The alarm threshold for temperature is manually set by the wearer of the invention, via a potentiometer control in the electrical circuitry of the invention. However, the alarm threshold for the galvanic skin resistance cannot be varied in the invention as described by McNamara.

U.S. Pat. No. 4,365,637 to Johnson discloses a self-contained wearable device which is applied to the wrist and which senses perspiration only. The device produces an audible indication when build up of perspiration on the skin causes the galvanic skin resistance between two electrodes to drop below a threshold. As disclosed, the threshold may be manually set by either of two means: by a potentiometer control in the electrical circuitry of the invention, or by screw adjustments which can variably displace the skin resistance electrodes away from the skin surface, thereby mechanically achieving a form of sensitivity control.

A limitation of devices described by McNamara and Johnson is they do not include automated means to compensate the apparatus for skin temperature or resistance variations arising from physiological responses not associated with hypoglycemia. If the manual threshold adjustments provided are not correctly set by the user, or if changes to the threshold adjustments are not made during the monitoring period to compensate for ongoing and non-symptomatic physiological variation, these devices may not detect an approaching hypoglycemic episode or, conversely, may produce a large number of annoying false alarms. Given the application of nocturnal monitoring, corrective threshold adjustments by the user are furthermore impractical.

The device disclosed by McNarama in U.S. Pat. No. 4,178,916 includes telemetry means for broadcasting the alarm signal to a nearby radio receiver. The Sleep Sentry™, a device manufactured by Teledyne Avionics of Charlottesville Va. and similar to the McNamara '916 device (but without telemetry means) has been clinically evaluated. In a home-based study of 24 pediatric patients conducted over 1444 patient-nights, Hansen et al. found that the Sleep Sentry™ produced a total of 192 alarms, 150 of the alarms being false and only 42 of which were deemed valid by means of Chemstrip bG value under 100 mg/dl in combination with hypoglycemic symptoms alleviated by subsequent feeding (Diabetes Care, 6:597–600 (1983)). A total of 46 hypoglycemic episodes were detected by the latter empirical triad, indicating that the Sleep Sentry™ produced at least four false negatives during the study.

In a subsequent clinical evaluation by Clarke et al. (Diabetes Care, 11:630–35 (1988)), only 10 of 18 adult diabetic subjects experienced an alarm from the Sleep Sentry™ during a 2-hour controlled infusion of insulin at 40 mU/(kghr), despite a mean plasma glucose nadir in the 50–53 mg/dl range as obtained by concurrent venous blood sampling. These results demonstrate how preset, non-adaptive thresholds for skin temperature and resistance in a monitoring device, such as described by McNamara or Johnson, may result in either false positive or false negative error rates that are unacceptably high, and consequently, such devices are not widely utilized.

A further limitation of inventions as disclosed by McNamara and Johnson is that DC current is applied to a pair of electrodes to determine the galvanic skin resistance. Even though the current may be only a few microamps, sensitive individuals may experience skin irritation after long exposure by means of iontophoresis. With the Teledyne Sleep Sentry™, iontophoretic irritation at the electrodes was observed by Hansen et al. in 6 of the 24 subjects participating in the study.

U.S. Pat. No. 4,509,531 to Ward discloses a personal physiological monitor similar to the invention of McNamara, buy the Ward device includes a temperature reference that is automatically established and which is updated periodically to accommodate slowly changing non-symptomatic skin temperature variations. Therefore, the temperature alarm threshold of the Ward invention is not manually preset to a single value but varies in response to discrete samples of the skin temperature itself. Further improvements include the use of pulsed current and enlarged electrodes to measure the galvanic skin resistance, thereby preventing skin irritation from iontophoresis due to the very low current density that is achieved.

A limitation of the invention disclosed by Ward is that the alarm threshold for perspiration represented by the galvanic skin resistance cannot be varied, this being the same limitation as described previously for the McNamara invention. As such, inventions disclosed by Ward and McNamara are incapable of compensating for non-symptomatic variations in perspiration, such as increasing perspiration which may be a hypothalamic thermoregulatory response to increasing core temperature. Although Johnson discloses manual means for adjusting the perspiration alarm threshold, the invention of Johnson is limited in that it does not automatically compensate for perspiration not associated with hypoglycemia.

Although improved when compared to the devices disclosed by McNamara and Johnson, the personal physiological monitor described by Ward has a number of additional limitations. Alarm indicia related to temperature are generated by the Ward invention only if the skin temperature drops a predetermined amount below the reference temperature. Since the predetermined amount cannot be varied, a hypoglycemic temperature drop smaller than the predetermined amount may go undetected. Conversely, if the predetermined amount is too small, false alarms may result from non-physiological temperature drops caused by air drafts or unconscious movement of the wrist to which the invention is applied.

The temperature reference is updated at arbitrary elapsed times as measured from device activation, rather than as required to compensate for any basal physiological process. As a result, the temperature reference may be inappropriately modified at a time when the skin temperature has dropped to a level incrementally above, but still not less than, the temperature alarm threshold derived from the reference, potentially resulting in an undetected hypoglycemic event.

Another limitation is that the first temperature reference is obtained immediately upon activating the monitor. Therefore, if the monitor is activated before sufficient time has elapsed to allow the device temperature to equilibrate with the skin temperature, an initial temperature reference which is falsely low may be obtained, resulting in reduced ability to detect a drop in skin temperature from the normative basal level. The temperature reference is acquired from a single sample of the skin temperature, and thus the temperature reference may be falsely high or low if the monitor was disturbed at the sample instant, for example, by body movement or environmental disturbance such as an air draft. Similarly, alarms are declared if a single instance of the skin temperature or resistance falls below the corresponding threshold, and so symptom detection can also be easily corrupted by transient disturbances such as air drafts or unconscious movement.

A final and practical limitation of the invention disclosed by Ward is that no means are provided to alert the user that internal batteries which power the monitor are approaching, but have not reached, full discharge. Therefore, it may be possible for a user to initially activate the device, but then experience unreliable operation after a few hours of continuous monitoring.

To overcome limitations of the prior art, one object of the present invention is to provide improved apparatus for detecting symptoms of hypoglycemia.

SUMMARY OF THE INVENTION

The invention relates to systems and methods for detecting symptoms of hypoglycemia in a diabetic individual. The system may comprise a temperature sensing system, a conductance sensing system, a trending system, a threshold system, and an alarm system. The temperature sensing system produces a temperature signal representative of a skin temperature of the diabetic individual. The conductance sensing system produces a conductance signal representative of a level of perspiration of the diabetic individual. The trending system produces a slope estimate representative of a rate of change of the skin temperature over a predetermined interval in response to the temperature signal. The threshold system produces a slope threshold representative of a hypoglycemic decline in skin temperature observed over the predetermined interval in response to the conductance signal and to the temperature signal. The alarm system produces an indication of the presence of hypoglycemic symptoms in response to the slope estimate and the slope threshold.

DESCRIPTION OF THE PREFERRED EMBODIMENTS

The embodiments illustrated herein are not intended to be exhaustive or to limit the invention to the precise form disclosed. The disclosed embodiments have been chosen and described in order to explain the principles, application, and practical use of the invention.

1. Construction of the Preferred Embodiments

Figure 1:
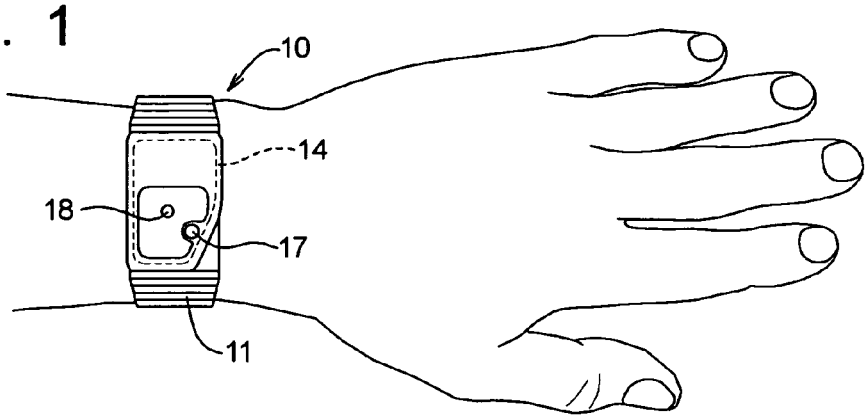
FIG. 1 is an elevation view of a first embodiment of the invention, as applied to a wrist of an individual to be monitored.
Figure 2:
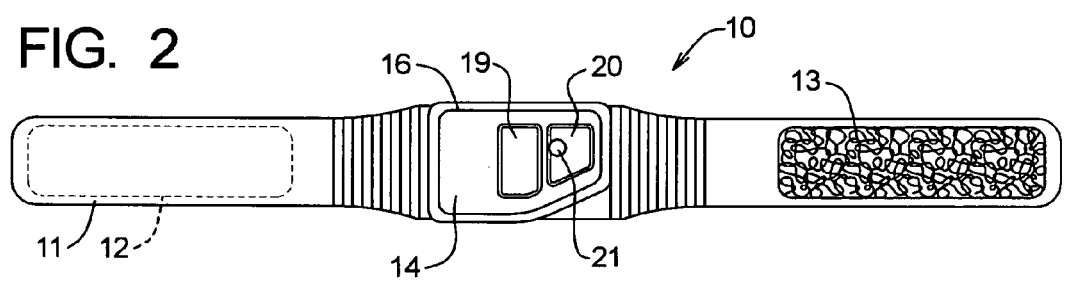
FIG. 2 is a bottom plan view of the device of FIG. 1 illustrating the surface of the invention which contacts the individual's skin.

Referring initially to FIGS. 1 and 2 of the drawing, depicted at 10 therein is a first embodiment of an apparatus for detecting symptoms of hypoglycemia. The example apparatus 10 includes an elastomeric wrist strap 11 on which a hook fabric strip 12, a loop fabric strip 13, and an electronics module 14 are supported. The strips 12 and 13 provide means for securing the electronics module 14 to a limb of a diabetic individual to be monitored.

Figure 3:
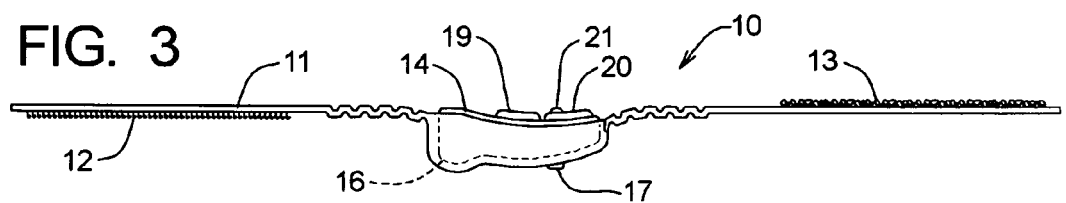
FIG. 3 is a side elevation view of the device of FIG. 1.
Figure 4:
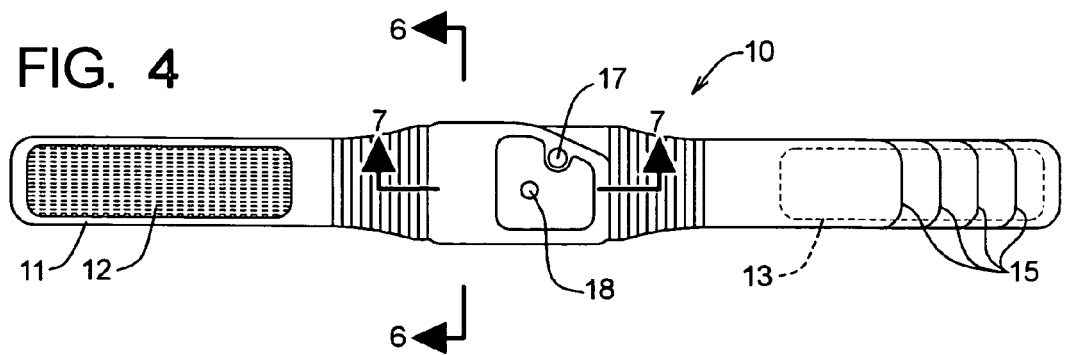
FIG. 4 is a top plan view of the device of FIG. 1 illustrating the side of the device disposed away from the surface of the individual's skin.

As shown in FIGS. 2, 3 and 4, the example strap 11 is injection-moulded as a single component from a hypoallergenic and conformable elastomer, with the strips 12 and 13 being bonded to the strap 11 by a thin layer of flexible adhesive (not shown) that is compatible with the elastomer from which the strap 11 is formed. Other strap configurations and materials may be used to support the electronics module 14, however.

The example the strap 11 may be cut with scissors at the locations of serrations 15, permitting the length of the strap 11 to be reduced so that the invention may be more readily filtered to limbs of smaller circumference. Elasticity and conformability of the strap 11 in combination with the fabric strips 12 and 13 allow the invention to be snugly fitted to the wrist as shown in FIG. 1, or to the ankle, or to any number of other locations on the upper or lower limbs of a varied population having broad distributions of size and weight.

FIGS. 2 and 3 illustrate that the strap 11 incorporates a stretchable recess 16 into which the electronics module 14 is inserted and held in place by elastic tension of the strap 11 around the perimeter of the module 14. The module 14 may be extracted from the strap 11 if desired. In particular, the application of moderate force to the strap 11 over the module 14 to elastically stretch the recess 16 allows the module 14 to be removed from the recess 16 in the strap 11.

FIGS. 3 and 4 show that an actuator 17 is moulded as part of the strap 11. As will be described in further detail below, the actuator 17 provides the individual being monitored with means for activating or de-activating the physiological monitoring function of the module 14. An orifice 18, which is also moulded as part of the strap 11, allows sounds emitted by the module 14 to reach the individual being monitored.

FIGS. 2 and 3 show that extending from the underside of the electronics module 14 are a positive electrode 19 and a negative electrode 20. When the strap 11 is applied at the wrist as shown in FIG. 1, or to another extremity such as the ankle, the electrodes 19 and 20 contact the skin and thereby provide means for sensing perspiration as represented in the skin conductance across the electrodes 19 and 20.

Figure 7:
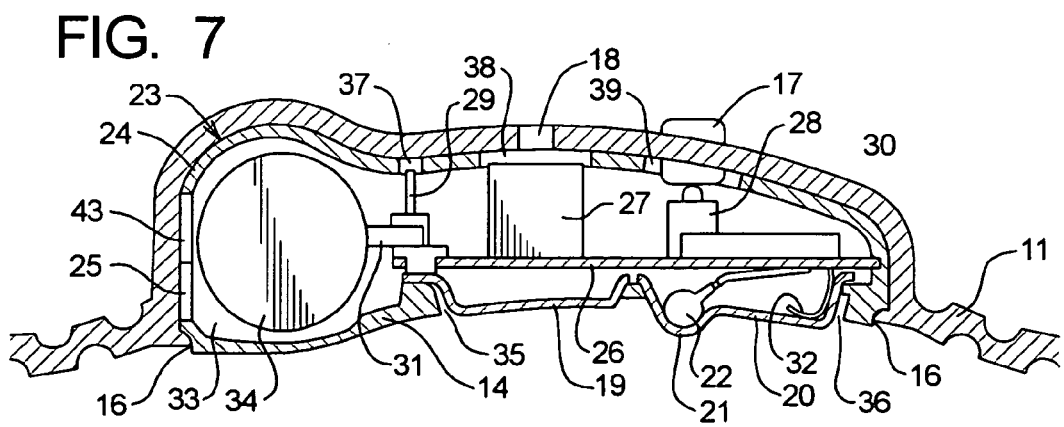
FIG. 7 is an end elevational sectional view of the wrist strap and electronics module of the invention shown in FIG. 4, illustrating disposition of a circuit board within wrist strap.

FIGS. 2, 3 and 7 further illustrate that the negative electrode 20 defines a dimple 21 to which a thermistor 22 is bonded. The thermistor 22 is bonded to the electrode 20 by a thermally-conductive adhesive. Thus the electrode 20, in combination with the thermistor 22, provide means for sensing the surface temperature of the skin at the same general location where the perspiration is sensed by the electrodes 19 and 20.

Figure 5:
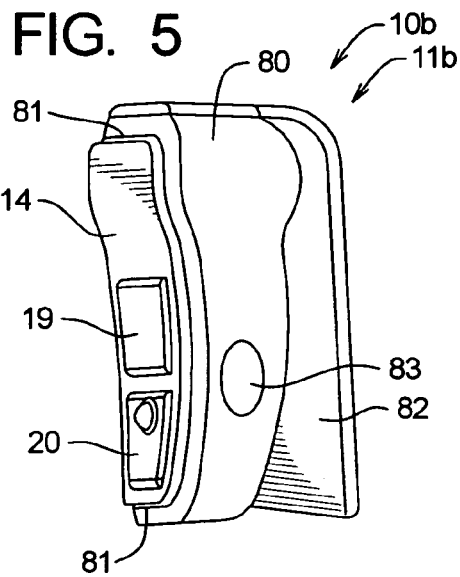
FIG. 5 is perspective view of a second embodiment of the invention that may be clipped to an article of clothing worn by an individual to be monitor.

Referring now to FIG. 5, depicted at 10b therein is a second embodiment of an apparatus for detecting symptoms of hypoglycemia. Instead of a strap, the apparatus 10b employs a garment clip structure 11b to situate the module 14 such that the electrodes 19 and 20 are disposed against a skin surface of the individual to be monitored. However, like the strap 11a described above, the clip structure 11b defines an elastomeric cup 80 that defines a stretchable recess 81 into which the electronics module 14 is inserted and held in place by elastic tension.

FIG. 5 illustrates that the clip structure 11b further comprises a plastic spring-clip member 82 is adhesively bonded to cup 80 provides means for affixing the apparatus to an article of clothing, such as an undergarment or sock, such that the electrodes 19 and 20 contact the skin of the wearer. To accommodate situation of the apparatus of FIG. 5 on a garment, an orifice 83 formed in the cup 80 provides unobstructed means for conveying sounds emitted by the module 14 to the individual being monitored.

In the example apparatus 10b, the module 14 is concealed from view as well as isolated from environmental disturbances such as air drafts which could cause the module 14 to produce false alarms. As such, the apparatus 10b of FIG. 5 may be utilized for monitoring during wakeful and active periods, such as while operating a motor vehicle, and thus potential muffling of sounds from orifice 83 by overlying clothing is anticipated and accommodated by the wearer.

Figure 6:
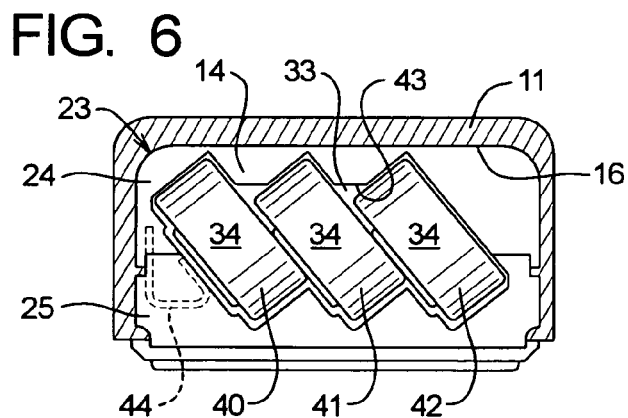
FIG. 6 is a sectional view of the wrist strap and electronics module of the invention shown in FIG. 4, illustrating disposition of a battery within the invention.

Referring now to the sectional views of FIGS. 6 and 7, it can be seen that an enclosure 23 of the electronics module 14 is formed by an upper housing member 24 and a lower housing member 25. The example housing members 24 and 25 are injection-moulded from a high-impact plastic and glued together by two-part epoxy adhesive.

Mounted within the enclosure 23 is a circuit board 26 that provides a substrate for the electronic circuitry of the invention. Soldered to the circuit board 26 are a speaker 27, a momentary pushbutton switch 28, an interface connector 29, a microcontroller 30, and a number of passive components which are omitted from FIG. 7 for clarity, but which appear in the electrical schematic of FIG. 8 and which will be described later. FIG. 7 also shows that the thermistor 22 connects to the circuit board 26. The electrodes 19 and 20 are also connected by spring contacts 31 and 32, respectively, to the circuit board 26.

As shown in FIGS. 6 and 7, the housing members 24 and 25 are shaped at one end to form a compartment 33 for a battery 34. The positive terminal of the battery 34 connects to the circuit board 26 via contact 31. In addition, FIGS. 6 and 7 show that the electrodes 19 and 20 shown in FIG. 7 extend or are accessible through holes 35 and 36, respectively, in the lower housing member 25. The example electrodes 19 and 20 are secured in place by a two-part epoxy adhesive. The adhesive also acts as a filling compound to create a water-tight seal around the electrodes 19 and 20.

FIG. 7 illustrates that the upper housing 24 defines holes 37, 38 and 39. The holes 37, 38, and 39 accommodate the connector 29, the speaker 27, and the actuator 17 respectively. As shown in FIG. 7, the actuator 17 of the strap 11 passes through hole 39 to abut the pushbutton switch 28. Note that the strap 11 covers the hole 37 so that the module 14 must first be removed from the strap 11, in the manner described previously, to allow access to the interface connector 29.

The sectional view of FIG. 6 shows that the battery 34 is comprised of three silver-oxide button cells 40, 41 and 42, which are installed in the compartment 33 through an access hole 43 formed by the housing members 24 and 25. A spring contact 44 connects the negative terminal of the battery 34 to the circuit board 26.

As shown in FIG. 6, the compartment 33 is shaped such that battery cells 40, 41 and 42 are tilted approximately 30 degrees from vertical, allowing the enclosure 23 to achieve a lower overall profile. FIG. 6 also shows that the compartment 33 and the hole 43 are shaped to preclude reversed polarity installation of cells 40, 41 and 42. As shown in FIG. 7, the hole 43 of the compartment 33 is covered by the strap 11, thereby retaining the cells 40, 41 and 42 of FIG. 6 in place.

When depleted, cells 40, 41 and 42 may be easily replaced. With the apparatus 10 removed from the individual, moderate force is applied to the strap 11 over the module 14 to elastically stretch the recess 16 and thereby eject the module 14 from the strap 11. The depleted cells 40, 41, and 42 may then be removed through the hole 43 of the compartment 33. Fresh cells are installed by reversal of the foregoing procedure. As such, battery replacement may be effected by an individual of limited skill and without the need for special tools in disassembly, or risk of error in battery installation and re-assembly.

Figure 8:
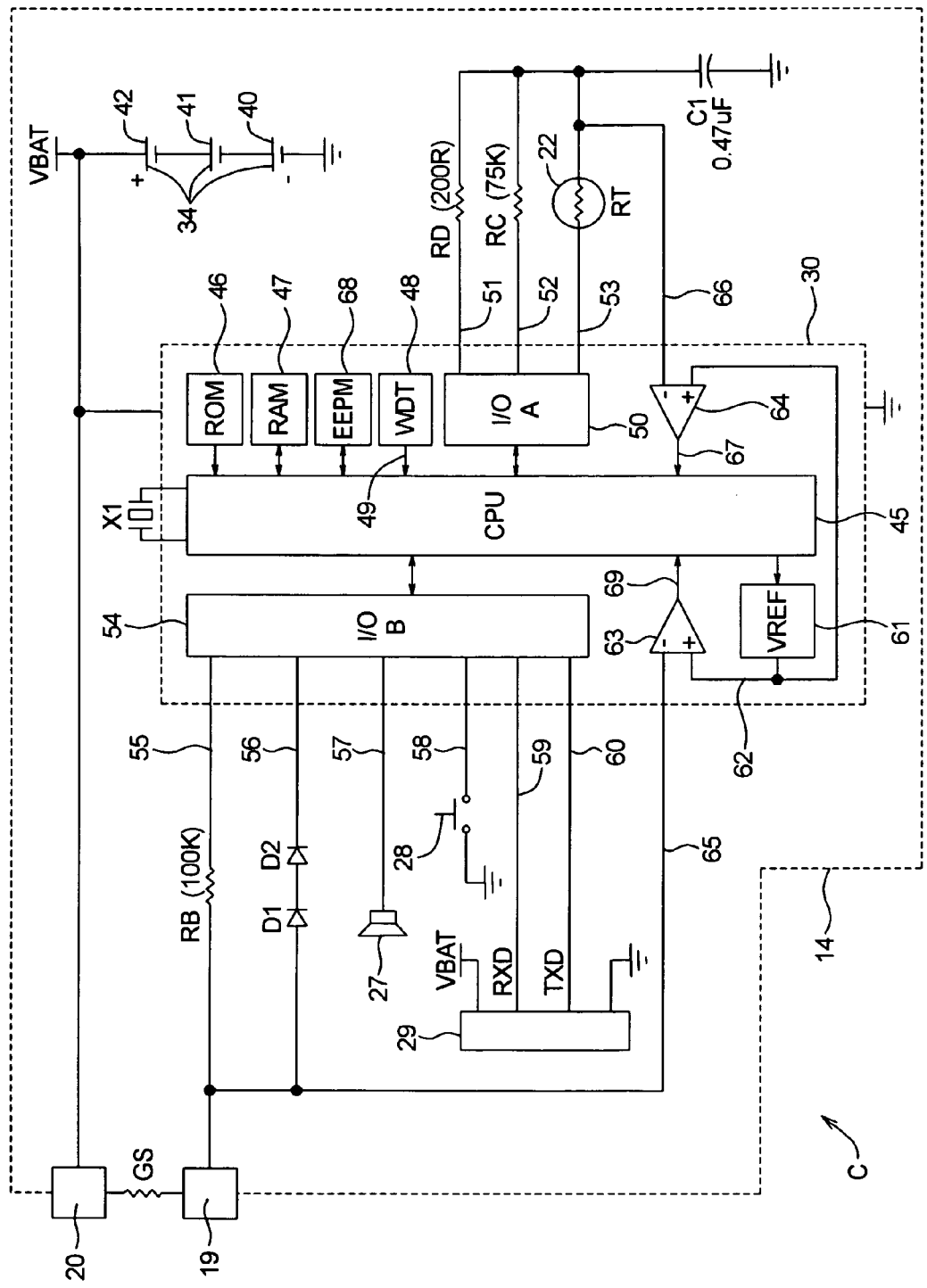
FIG. 8 is a schematic block diagram of the electrical circuitry of the device of FIG. 1.

FIG. 8 is a schematic block diagram of an electrical circuit C contained within the module 14 appearing in FIGS. 1 through 7. The example microcontroller 30 is a CMOS integrated circuit comprising the following functional elements: a central processing unit (CPU) 45, a read-only memory (ROM) 46, a random-access memory (RAM) 47, electrically-erasable programmable memory (EEPM) 68, a watchdog timer (WDT) 48, an first input/output port 50, an second input/output port 54, and a programmable voltage reference (VREF) 61.

The CPU 45 executes a sequence of instructions according to the program stored in the ROM 46. The RAM 47 provides the CPU 45 with means for temporary data storage. The EEPM 68 provides the CPU 45 with means for non-volatile data storage. The WDT 48 outputs a periodic interrupt signal 49 to the CPU 45. The first input/output port 50 allows the CPU 45 to input or output signals 51, 52 and 53 respectively. The second input/output port 54 allows the CPU 45 to input or output signals 55, 56, 57, 58, 59 and 60 respectively.

Under the control of the CPU 45, the VREF 61 outputs the signal 62 to analog comparators 63 and 64. As shown in FIG. 7, the comparator 63 responds to a divider signal 65 and outputs a comparator the signal 69 to the CPU 45, and the comparator 64 responds to a charge signal 66 and outputs a timing signal 67 to the CPU 45.

The speaker 27 is schematically shown in FIG. 8 as being responsive to output signal 57 of the port 54. The switch 28 produces the control signal 58 which is conveyed to the CPU 45 by means of the port 54. The thermistor 22 of FIG. 7, schematically indicated in FIG. 8 and also designated by its resistance value RT, is controlled by signal 53 of the port 50.

The electrodes 19 and 20 of FIG. 7 are also schematically represented in FIG. 8, the positive electrode 19 being connected to positive terminal VBAT of the battery 34, and the negative electrode 20 outputting the divider signal 65 to the comparator 63. The skin conductance of the individual being monitored is indicated in FIG. 8 as GS, which bridges the electrodes 19 and 20. The interface connector 29 of FIG. 7 appears schematically in FIG. 8 as providing four signals: VBAT; The RXD signal 59; TXD signal 50; and circuit ground, respectively. The RXD signal 49 and the TXD signal 50 are serial data communication signals respectively conveyed to or from the CPU 45 by means of the port 54.

FIG. 8 illustrates a number of additional components of the circuit C. A discharge resistor RD provides means for discharging capacitor C1 via signal 51 under control of the CPU 45. A calibration resistor RC charges capacitor C1 under control of the CPU 45 via signal 52. A divider resistor RB, under control of the CPU 45 via the signal 55, allows the CPU 45 to measure skin conductance between the electrodes 19 and 20. Diodes D1 and D2, under control of the CPU 45 via the signal 56, provide means of clamping the signal 65 to a fixed voltage level. A crystal X1 sets the operating frequency of the CPU 45 and facilitates the measurements of time intervals by the CPU 45.

According to FIGS. 1 through 8 inclusive, a working model of the preferred embodiment of the invention can be assembled by persons skilled in the art using the following components: the thermistor 22 is QTMC-43 manufactured by Quality Thermistor Inc. of Boise Id.; the speaker 27 is QMB-105P supplied by Star Micronics Co. of Edison N.J.; the switch 28 is TL3302 manufactured by E-Switch of Brooklyn Park N.J.; cells 40, 41, and 42 are each Type 357 manufactured by Eveready Battery Co. of St. Louis Mo.; and the microcontroller 30 is PIC16CE625-04/SS manufactured by Microchip Technology Inc. of Chandler Ariz. For the microcontroller 30 as specified, the corresponding capacities of the ROM 46, the RAM 47 and the EEPM 68 are 2K words, 128 bytes, and 128 bytes respectively.

In a working model of the preferred embodiment, the strap 11 is injection-moulded from a hypoallergenic and conformable elastomer such as Santoprene™ Hook fabric strip 12 is Velcro™ 5163126 and loop fabric strip 13 is Velcro™ 5163125, strips 12 and 13 being bonded to the strap 11 by #480 adhesive manufactured by Loctite Corp. of Rocky Hill Conn. The electrodes 19 and 20 are progressive die-formed from stainless steel 316L material of 0.025" thickness. The thermistor 22 is bonded to the electrode 20 with #383 thermal adhesive, also manufactured by Loctite Corp. Upper housing 24 and lower housing 25 are injection-moulded from high-impact plastic material such as GE Lexan™ type 124. Spring contacts 31, 32 and 44 are progressive die-formed from phosphor bronze material of 0.010" thickness, and are then nickle plated to inhibit oxidation and improve solderability.

One of ordinary skill in the art will recognize that other components and circuit configurations may be used to construct a device according to the principles of the present invention.

2. Operation of the Preferred Embodiments

The apparatuses 10 and 10a assembled as described above are intended for use by a diabetic individual who, when asleep, wishes to be awakened when physiological symptoms indicative of hypoglycemia are detected. Symptoms indicative of hypoglycemia, or "insulin shock", include increased perspiration, a drop in skin surface temperature, or both physiological conditions simultaneously. The apparatus 10a differs from the apparatus 10 only in the manner in which the apparatus is supported next to the user's skin, so only the apparatus 10 will be described in detail below.

The example apparatus 10 described above is applied to the wrist as shown in FIG. 1, or to another site, after which the electronics module 14 is activated by means of the actuator 17. The diabetic individual may then sleep while the module 14 continues to periodically monitor conductivity and temperature of the skin in contact with the electrodes 19 and 20.

When an increase in perspiration causes a corresponding detectable increase in conductance GS across the electrodes 19 and 20, or when a detectable drop in skin temperature at the electrode 20 occurs, the module 14 produces an audio alarm via the speaker 27 to alert the wearer to the symptoms of hypoglycemia.

As will be described in further detail below, the apparatus embodies means for detecting an increase in perspiration or drop in skin surface temperature signifying a hypoglycemic condition, as distinct from variations in basal perspiration and temperature arising from physiological behaviour not related to blood glucose concentration. To accommodate the potential range of normal physiological and hypoglycemic responses, the invention may be set to function in any one of a plurality of operating modes, each mode of the plurality being embodied as an individual algorithm within the program of instructions contained in the ROM 46 of the microcontroller 30. A description of said operating modes and their application in use of the invention will now be provided, wherein reference will be made throughout to the block diagram of FIG. 8.

2.1 Basic System Functions

Operation of the invention is largely defined by individual subroutines of instructions contained in the ROM 46. The subroutines executed by the CPU 45 form the basis for a simple real-time operating system. The CPU 45 responds to three interrupt sources: the periodic interrupt signal 49 produced by the WDT 48; the control signal 58 produced by the switch 28; and The RXD signal 59. The RXD signal 59 is a serial data communications signal conveyed by the interface connector 29 from an externally-connected device, such as a personal computer.

Elements of the operating system in the ROM 46 correspond to a single-button user interface provided by the switch 28 and the speaker 27; a serial communications interface implemented through signals 59 and 60; and means provided by the microcontroller 30 for measuring time intervals, skin temperature, and skin conductance or perspiration.

Referring again to FIG. 8, the microcontroller 30 is connected to the battery 34 and as such is continuously energized by the battery 34. The CPU 45 remains in an inactive state until the CPU 45 receives an interrupt conveyed by signals 49, 58 or 59 as described above. Upon receiving an interrupt, the CPU 45 becomes active and executes corresponding subroutines of instructions contained in the ROM 46, returning to the inactive state when said subroutines have been executed.

Because the microcontroller 30 is a CMOS device, the CPU 45 in the inactive state draws essentially no current from the battery 34, although status of signals output by ports 50 and 54, and the data contents of the RAM 47 and the EEPM 68, are maintained in the state established by the CPU 45 in executing the subroutines of the ROM 46. The average current drawn from the battery 34 is thereby limited to a few microamps as required by the WDT 48, which runs continuously. In a working model of the preferred embodiment, the cells 40, 41, and 42 may be Type 357 batteries, which provide sufficient capacity to continuously power the circuitry of FIG. 8 for 6 to 10 months under typical usage conditions.

2.1.1 Single-Button User Interface

The WDT 48 outputs the interrupt signal 49 to the CPU 45 such that the CPU 45 is periodically activated once every 2.3 seconds, nominally. If the invention is not monitoring a diabetic individual when the signal 49 is received by the CPU 45, the CPU 45 immediately returns to the inactive state.

To initiate monitoring of a diabetic individual, the strap 11 containing the module 14 is applied to an extremity, for example the ankle, or the wrist as illustrated in FIG. 1. Referring to FIG. 7, the actuator 17 is then depressed, causing the strap 11 to elastically deflect and the switch 28 to be thereby actuated. Referring to FIG. 8, the switch 28 produces the control signal 58 to the CPU 45 via the port 54, activating the CPU 45. The CPU 45 drives the speaker 27 via output signal 57 of the port 54 to produce an audible tone indicative of the activation of the module 14, after which monitoring functions for skin temperature and perspiration are initiated as will be described later.

While monitoring of skin temperature and perspiration is ongoing, the diabetic individual may elect to deactivate the module 14 at any time and thereby end the monitoring process. This is accomplished by holding down the actuator 17 of the strap 11 for a predetermined length of time, for example two seconds, to signal the CPU 45 via the switch 28 that the user wishes to deactivate the module 14. The CPU 45 responds to the interrupt from the switch 28 by driving the speaker 27 via the port 54 to emit an audible deactivation tone.

The user must then respond to the deactivation tone by releasing the actuator 17 and then depressing and releasing the actuator 17 quickly and twice within an additional and shorter predetermined interval, for example 600 milliseconds. The CPU 45 monitors for this activation pattern by means of the switch 28 producing signal 58. If the actuator 17 is not activated twice within the 600 millisecond interval, the speaker 27 stops emitting the deactivation tone and the module 14 returns to monitoring.

To initiate a subsequent deactivation request, the user must release the actuator 17, and then hold down the actuator 17 for the required two-second interval. Thereby, accidental, unconscious or otherwise non-deliberate deactivation of the invention is prevented, such as might be the case if only a single depression of the actuator 17 was necessary to end monitoring.

In the event that a symptom of hypoglycemia is detected during the monitoring period, the CPU 45 produces an audible alarm indication to awaken the user by driving the speaker 27 via the port 54. Regardless of subsequent changes in the status of the symptom detected, the CPU 45 latches the alarm condition and the sound emitted by the speaker 27 cannot be disabled until the individual being monitored responds by means of the actuator 17 of the strap 11.

To inhibit the audio alarm emitted by speaker 17 and deactivate the module 14, the actuator 17 is depressed and released quickly and twice within a predetermined interval, such as 600 milliseconds. The CPU 45 monitors for this pattern by means of the switch 28 producing signal 58. If the actuator 17 is not activated twice within the 600 millisecond interval, the speaker 27 continues to emit the audible alarm. Similar to deactivation of the monitoring function, accidental, unconscious or otherwise non-deliberate deactivation of the alarm is thereby prevented.

2.1.2 Time Interval Measurement

Measurement of time intervals is central to operation of the invention. Throughout the operating system being described, short intervals (i.e., having a duration less than the period of the signal 49 from the WDT 48) are measured by the CPU 45 through the counting of instruction execution cycles (i.e. software timing loops). Short timing intervals are therefore related in absolute terms to the frequency of crystal X1, and can be obtained with a high degree of precision and repeatability.

Longer durations, which are measured in terms of minutes or hours, are derived by the CPU 45 counting interrupts as conveyed by the signal 49 from the WDT 48. Each interrupt occurs approximately once every 2.3 seconds. Because the WDT 48 in a working model of the preferred embodiment corresponds to a simple R-C oscillator, a wide tolerance in the period of the signal 49 is experienced in practise, particularly in terms of unit-to-unit variations of the microcontroller 30.

To overcome this limitation, the CPU 45 measures the period of the signal 49 respect to the frequency of crystal X1 upon initial activation of the module 14 as described in section 2.1.1, and in accordance with the method disclosed by D'Souza in technical bulletin TB004, "Automatic Calibration of the WDT Time-Out Period", published by Microchip Technology Inc. of Chandler Ariz. (1996). Thereby, the CPU 45 determines a calibration factor for the WDT 48 which is then stored in the RAM 47, and which is later applied in determination of any duration exceeding a few seconds.

2.1.3 Skin Temperature Measurement

Once the module 14 has been activated to begin monitoring as described in section 2.1.1, the CPU 45 periodically obtains a temperature signal TS(n) representative of the skin temperature of the diabetic individual at sample instants n, where n corresponds to time as measured in interrupts produced by the WDT 48. In deriving TS(n), the CPU 45 controls discharge resistor RD, calibration resistor RC and capacitor C1 of FIG. 8 via the port 50, in accordance with the signal waveform diagram of FIG. 9, and in a manner similar to the method disclosed by Cox in application note AN512, "Implementing Ohmmeter/Temperature Sensor", published by Microchip Technology Inc. of Chandler Ariz. (1997).

Referring again to FIGS. 8 and 9, signals 51, 52 and 53 output from the port 50 are maintained at low logic level between interrupts produced by the WDT 48, the time interval between two successive interrupts being indicated in FIG. 9 as $t_{WDT}$. Thereby, capacitor C1 is discharged so that the charge signal 66 is at zero volts. On odd-numbered interrupts from the WDT 48, a single example of which is represented by pulse 70 of the interrupt signal 49 shown in FIG. 8, the CPU 45 configures programmable voltage reference the VREF 61 to output signal 62 equal to a predefined fraction of battery voltage VBAT. The CPU 45 then changes the configuration of the port 50 so that signal 53 is input rather than output, and sets signals 51 and 52 to a high logic level.

Because signal 53 is now an input and signal 51 corresponds to an open-drain output terminal of the port 50, signals 51 and 53 thereby follow the charge signal 66 as capacitor C1 is charged through calibration resistor RC. According to FIG. 9 and as described in section 2.1.2, the CPU 45 measures time interval $t_{RCAL}$ required for signal 66 to reach signal 62, as indicated by a transition in the timing signal 67 from a high to a low state.

Once the interval $t_{RCAL}$ is determined and saved to the RAM 47, the CPU 45 then changes configuration of the port 50 so that signal 53 is output and sets signals 51, 52 and 53 low. According to FIG. 9, capacitor C1 is thereby rapidly discharged into the port 50 through RD, RC and RT in parallel so that signal 66 returns to zero volts. While capacitor C1 discharges, the CPU 45 returns to the inactive state in which little or no current is drawn from the battery 34 by the CPU 45.

Figure 9:
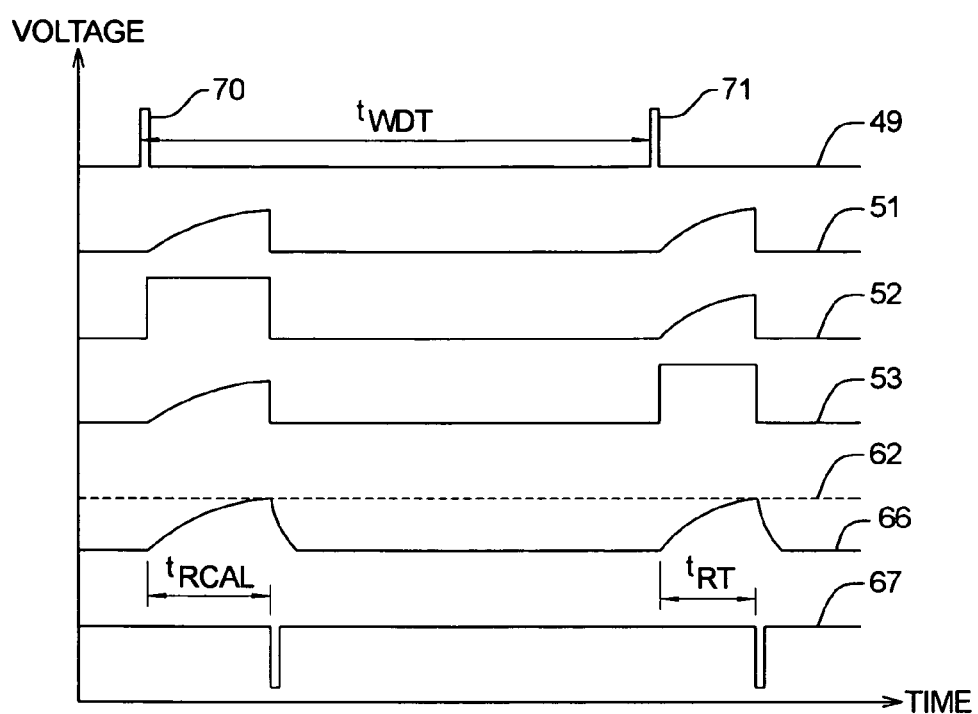
FIG. 9 is a waveform diagram illustrating signals generated by the circuit of FIG. 8.

On even-numbered interrupts from the WDT 48, a single example of which is represented by pulse 71 of the interrupt signal 49 shown in FIG. 9, a similar procedure to that described immediately above is performed by the CPU 45 to determine interval $t_{RT}$, except in this case capacitor C1 is charged through resistance RT, corresponding to the thermistor 22.

To obtain $t_{RT}$, the port 50 is configured so that signal 52 is input rather than output, and signals 51 and 53 are set high until the charge signal 66 reaches signal 62 as indicated by a high-to-low transition of the timing signal 67 from the comparator 64. Once having determined and saved interval $t_{RT}$ to the RAM 47, the CPU 45 then configures the port 50 so that the signal 52 is output, and sets signals 51, 52 and 53 low to discharge capacitor C1. According to the corresponding subroutine in the ROM 46, the CPU 45 then calculates the thermistor resistance RT as:

$$RT = RC * t_{RT}/t_{RCAL} \tag{1}$$

where $t_{RCAL}$ and $t_{RT}$ are the intervals obtained by the method described above.

Upon deriving RT, the CPU 45 obtains a corresponding temperature TS(n) by accessing a calibration lookup table contained in the non-volatile memory EEPM 68, the lookup table providing resistance values corresponding to temperature of the thermistor 22. Table I is an example lookup table that may be programmed into the EEPM 68 in a working model of the preferred embodiment, the working model having the thermistor 22 as specified earlier (QTMC-43).

TABLE I

| Resistance RT (kohm) | Temperature TS (° C.) |
|---|---|
| 105.5 | 24.00 |
| 95.78 | 26.00 |
| 86.81 | 28.00 |
| 78.65 | 30.00 |
| 71.29 | 32.00 |
| 64.74 | 34.00 |
| 58.99 | 36.00 |
| 54.05 | 38.00 |
| 49.68 | 40.00 |

To obtain a temperature TS(n) corresponding to resistance RT calculated according to (1), the CPU 45 searches the lookup table of the EEPM 68 and locates the two nearest neighboring values of resistance, then performs a linear interpolation to produce a result TS(n) having a resolution of 0.01° C. The CPU 45 further processes the temperature signal TS(n) as directed by instructions in the ROM 46, and may produce an alarm by means of the speaker 27 according to section 2.1.1, given that conditions to be described in section 2.2.1 are satisfied. Otherwise, upon completing the calculations, the CPU 45 returns to the inactive state in which little or no current is drawn from the battery 34 by the CPU 45.

As is evident from equation (1), the method disclosed for obtaining RT and thus TS(n) is advantageously insensitive to tolerance or drift in capacitor C1 or signal 62 as derived by the VREF 61 from VBAT of the battery 34. In a working model of the preferred embodiment, interval $t_{WDT}$ is nominally 2.3 seconds such that temperature signal TS(n) is periodically obtained by the CPU 45 every 4.6 seconds, approximately.

With values shown in FIG. 8 for capacitor C1 and resistors RD and RC, and with the thermistor 22 as specified previously, interval $t_{RCAL}$ is nominally 32 milliseconds, and $t_{RT}$ typically ranges from 23 to 45 milliseconds, depending on the temperature of the thermistor 22 and its corresponding resistance RT. Therefore, including time required to perform subsequent calculations, the CPU 45 is active for nominally 4 to 5% of interval $t_{WDT}$, advantageously achieving very low power consumption from the battery 34.

2.1.4 Skin Conductance Measurement

Once the module 14 has been activated to begin monitoring as described in section 2.1.1, and in addition to producing a temperature signal TS(n) representative of the skin temperature as described in section 2.1.3, the CPU 45 periodically obtains a conductance signal GS(n) representative of the level of perspiration of the diabetic individual at sample instants n, where n corresponds to time as measured in interrupts produced by the WDT 48.

Referring to FIG. 8, the signal 55 output by the port 54 is maintained at a high logic level between interrupts produced by the WDT 48. Therefore, the signal 55 is essentially at the same potential as the battery potential VBAT, and so no current flows from the electrode 19 to the electrode 20 through the skin conductance GS. The signal 56 output by the port 54 is also maintained at a high logic level so that diodes D1 and D2 remain reverse-biased.

On odd-numbered interrupts from the WDT 48, a single example of which is represented by pulse 70 of the signal 49 in FIG. 9, the CPU 45 performs additional operations after determining interval $t_{RCAL}$, in accordance with instructions contained in the ROM 46. The CPU 45 causes the port 54 to set the signal 55 to a low logic level, thereby causing the divider signal 65 less than VBAT to be established at the comparator 63 by means of the voltage divider created by resistor RB and skin conductance GS.

As controlled by the CPU 45, programmable voltage reference the VREF 61 outputs signal 62 as an increasing staircase ramp comprised of discrete voltage levels, until the CPU 45 determines that signal 62 equals or exceeds signal 65 by means of a high-to-low transition in the signal 69 as output by the comparator 63. At this point, the potential V62 of signal 62 is described by:

$$V62 \geq (VBAT*GS)/(GS+GB) \quad (2)$$

where conductance GB is 1/RB. In the preferred embodiment, signal 62 is ratiometrically derived from VBAT by the VREF 61, so that potential V62 is also described by:

$$V62 = VBAT*bR/aR \quad (3)$$

where aR corresponds to the control value written to the VREF 61 by the CPU 45 to produce an output V62=VBAT, and where bR <=aR is the control value written to the VREF 61 by the CPU 45 such that equation (2) is satisfied. Combining (2) and (3) for the case of equality produces:

$$GS(n) = GB*(bR/aR-bR) \quad (4)$$

By the method described above, upon determining the smallest value bR for the VREF 61 such that the signal 69 from the comparator 63 is a low logic level, the CPU 45 restores the signal 55 to a high logic level so that current no longer flows through the skin. The CPU 45 then calculates equation (4) and thereby obtains a conductance signal GS(n) directly representative of the level of perspiration underneath the electrodes 19 and 20.

After obtaining the skin temperature signal TS(n) on the following even-numbered interrupt (e.g. pulse 71 of the signal 49 in FIG. 9), the CPU 45 further processes conductance signal GS(n) as directed by instructions in the ROM 46, and may produce an alarm by means of the speaker 27 according to section 2.1.1, given that conditions to be described in section 2.2.2 are satisfied. Otherwise, upon completing the calculations, the CPU 45 returns to the inactive state in which little or no current is drawn from the battery 34 by the CPU 45.

As is evident from equation (4), the method disclosed for obtaining GS(n) is advantageously insensitive to tolerance or drift in the potential VBAT of the battery 34. In a working model of the preferred embodiment, the VREF 61 may be set by the CPU 45 to output one of 16 discrete voltage levels in steps equal to VBAT/24 volts, and thus in equation (4) parameter aR=24 and bR may range from 0 to 15. Interval $t_{WDT}$ is nominally 2.3 seconds such that conductance signal GS(n) is periodically obtained by the CPU 45 every 4.6 seconds, approximately. The CPU 45 sets the signal 55 to a low logic level for 4.0 milliseconds when determining bR of equation (4), and thus the average current density imposed on the skin surface by the electrodes 19 and 20 is very small, on the order of a few nanoamps. Advantageously, power consumed from the battery 34 is thereby minimized, and risk of inducing skin irritation by iontophoresis at the electrodes 19 and 20 is also minimized.

2.1.5 Battery Test

A process similar to the method described in section 2.1.4 for determining conductance signal GS(n) is executed by the CPU 45 to test the potential VBAT of the battery 34. The battery test is performed by the CPU 45 once, when the module 14 is initially activated as described in section 2.1.1, and prior to initiating measurement of skin temperature TS(n) and conductance GS(n) as described in sections 2.1.3 and 2.1.4 respectively.

Referring to FIG. 8, the CPU 45 maintains the signal 55 at a high logic level and sets the signal 56 to a low logic level. Thereby, diodes D1 and D2 become forward biased by resistor RB, establishing a predetermined reference level for signal 65 which is largely independent of the battery potential VBAT. The CPU 45 controls VREF 51 to output signal 62, voltage V62 of signal 62 being ratiometrically derived from the battery potential VBAT as given by equation (3).

Comparator 63 compares the reference voltage established by diodes D1 and D2 to signal 62 output by the VREF 61. The CPU 45 tests the signal 69 output by the comparator 63, the signal 69 corresponding to a high logic level if VBAT is sufficient to operate the circuit of FIG. 8 continuously and reliably for at least 12 hours, and low otherwise. After testing the signal 69, the CPU 45 returns the signal 56 to a high logic level so that diodes D1 and D2 remain reversed-biased and thereby have no influence on subsequent measurement of conductance signal GS(n).

In the event that the signal 69 observed during the battery test corresponds to a high logic level, operation of the module 14 in monitoring skin temperature TS(n) and conductance GS(n) proceeds as described above. In the event that the signal 69 is found low during the battery test, the CPU 45 drives the speaker 27 via signal 57 to produce an audible alarm indicative of the low battery potential. Operation of the module 14 in monitoring skin temperature and conductance is inhibited in this case as the potential VBAT of the battery 34 is insufficient to provide reliable operation.

The audible alarm is deactivated by a single depression of the actuator 17, as conveyed to the CPU 45 by signal 58 of the switch 28. Thereby, the invention includes alarm means to produce an indication of depleted the battery 34 when battery potential VBAT as conveyed through the VREF 61 falls below a predetermined battery alarm threshold, the threshold being signal 65 established by forward-biased diodes D1 and D2. Referring to FIGS. 6 and 7, exhausted cells 40, 41 and 42 may then be replaced after ejecting the module 14 from wrist the strap 11, according to the procedure described in section 1.

2.1.6 Serial Communications Interface

Referring back to FIGS. 6 and 8, the invention provides a communications interface by means of the interface connector 29, which allows data to be serially conveyed either to or from an externally-connected device such as, for example, a personal computer. To access the connector 29, the module 14 must first be removed from wrist the strap 11 according to the procedure given previously in section 1. As such, the communications interface is normally concealed from the typical diabetic user of the invention, and is provided primarily to facilitate automated testing during manufacture, and temperature calibration of the thermistor 22.

As the microcontroller 30 does not provide a universal asynchronous receiver-transmitter (UART) as part of its hardware subsystem, a UART is emulated by the CPU 45 executing corresponding subroutines in the ROM 46. Methods for implementing such emulation are described by Palacherla in application note AN510, "Implementation of an Asynchronous Serial I/O" published by Microchip Technology Inc. of Chandler Ariz. (1997).

Referring to FIG. 8, a transition in The RXD signal 59 from an externally-connected device produces an interrupt which is conveyed to the CPU 45 by means of the port 54. The interrupt activates the CPU 45 to decode the serial bit stream conveyed by signal 59 and thereby produce a byte which is stored in the RAM 47, this byte typically corresponding to an ASCII character. The character obtained is interpreted by the CPU 45, subsequently causing one of a number of procedures to be executed according to instructions in the ROM 46, these procedures including:

a. Accept the following byte received via The RXD signal 59 as the operating mode of the invention, and program this operating mode into the non-volatile memory EEPM 68.
b. Serially transmit an ASCII character representative of the current status of the module 14 (idle; monitoring; or alarmed) by means of TXD signal 60.
c. Serially transmit the most current value of the skin temperature TS(n), obtained according to section 2.1.3 above, by means of TXD signal 60.
d. Serially transmit the most current value of the skin conductance GS(n), obtained according to section 2.1.4 above, by means of TXD signal 60.
e. Accept the following block of data bytes received via The RXD signal 59 as a calibration lookup table for the thermistor 22, and program the table into the EEPM 68. An example of such data appears in Table I of section 2.1.3.

Upon executing the required procedure, the CPU 45 returns to the inactive state in which little or no current is drawn from the battery 34, until a subsequent interrupt from WDT 38, the switch 28, or The RXD signal 59 activates the CPU 45 as described previously.

The serial communications interface may be advantageously applied to automated calibration of the thermistor 22 during volume production of the invention. In principle, an automated temperature controller incorporating a small heating device and a calibrated, traceable temperature gauge applies preselected temperatures to the module 14 at the electrode 20. Temperature signal TS(n) corresponding to each applied temperature is obtained from the module 14 by the temperature controller via the serial communications interface as described above. The temperature controller applies a least-squares curve fit to the TS(n) data acquired and thereby generates a lookup table similar to Table I of section 2.1.3, which is then transmitted to the module 14 by means of the serial interface for storage in the non-volatile memory EEPM 68.

2.2 Detection of Hypoglycemic Symptoms

Basic system functions described in section 2.1 provide means for activating and deactivating the invention, for producing an alarm indication, for calibrating the thermistor 22, for producing a temperature signal TS(n) representative of a skin temperature, and for producing a conductance signal GS(n) representative of a level of perspiration. In a working model of the preferred embodiment, methods disclosed periodically produce paired values of TS(n) and GS(n) every 4.6 seconds, approximately. Given each pair of samples TS(n) and GS(n), further processing is applied by the CPU 45 of FIG. 8 as directed by subroutines in the ROM 46, and an alarm indication may be produced indicating the presence of hypoglycemic symptoms if certain conditions are met, as will be now described.

Detection methods employed in the present invention are based on a hypothesis that autonomic responses associated with basal or "background" physiology, such as the thermoregulatory system which maintains core body temperature at a nominal 37° C., occur slowly compared to the autonomic stress response attributable to hypoglycemia. Distinction between basal physiology and adrenergic response is accomplished in the present invention through determination of the rate of change of observed physiological variables.

By deriving such trend information, distinction may also be made between adrenergic responses and artifactual signals which occur too quickly to be possibly associated with human physiology. For example, and as will be described in detail below, by deriving the trend of the skin temperature through linear regression of collected data, the present invention is able to distinguish a decline in skin temperature due to hypoglycemia from a decline due to autonomic regulation of core body temperature, and is also able to distinguish a hypoglycemic decline in skin temperature from an artifactual decline induced by a change in ambient environmental conditions. Thereby, the present invention improves on prior art which directly compares physiological variables to invariant threshold levels.

Classification of a physiological variable as indicative of a condition, or not indicative, ultimately requires comparison of the variable to a defining threshold. Another aspect which distinguishes the present invention from prior art is that such decision thresholds are made adaptive to confounding observations which, if not accounted for, may result in an erroneous classification. For example, and as will be described in detail below, the present invention increases the perspiration detection threshold as skin temperature increases, the expectation being that perspiration observed in this case will be attributable to autonomic regulation of core body temperature, and not attributable to hypoglycemia.

2.2.1 Detection of Hypoglycemic Skin Temperature Symptoms

In very general terms, and given that the individual under observation exhibits the symptom, a decline in skin temperature induced by a discernable adrenergic response to hypoglycemia (i.e. BG<60 mg/dL) is broadly characterized as a decrease on the order of 1° C. to 3° C., starting at a nominal or basal skin temperature in the range of 30° C. to 35° C., as observed over a time interval spanning 15 to 30 minutes.

The cumulative percentage change in the observed physiological variable due to the symptom is therefore relatively small, on the order of −6%, and observation intervals necessary to clearly identify the symptom are measured in terms of minutes to hours. As described previously, the skin temperature signal TS(n) is obtained by the CPU 45 of FIG. 8 approximately once every 4.6 seconds in a working model of the preferred embodiment. Therefore, the data interval of TS(n) is short when considering rise and fall times observed in actual skin temperature, particularly when considering the observation interval needed to reliably detect the hypoglycemic symptom.

Given the limited memory capacity of the microcontroller 30 of FIG. 8 for storage of past data samples, it is necessary to re-sample the temperature signal TS(n) at a rate more suitable to the frequency characteristics of the skin temperature variation. A simple approach is described as follows:

$$T(k)=TS(n), k=n/M \qquad (5)$$

where the integer division in equation (5) truncates the fractional part of index k, and thereby, the skin temperature signal T(k) is obtained from every Mth sample of signal TS(n). There are limitations to this simple approach due to temperature disturbances, such as air drafts or body movement, which may corrupt individual samples of TS(n).

Given the potential for noise in TS(n), the preferred embodiment has the CPU 45 of FIG. 8 obtain T(k) through calculation of the sample mean over MT points:

$$T(k) = \sum_{j=0}^{j=M_T-1} TS(n-j)/M_T \qquad (6)$$

where, as in (5), sample index k thereby increments once for every $M_T$ samples of signal TS(n). In the working model of the preferred embodiment, $M_T$ is determined from a calibration factor derived for the period of WDT 38 according to the method of section 2.1.2, so that the data interval of skin temperature signal T(k) is nominally 30 seconds, this being a more suitable sampling period for observing the skin temperature. For the microcontroller 30 of FIG. 8 having a WDT 38 with nominal 2.3 second period, $M_T$ is typically 6 or 7.

At each sample instant k, a slope estimate of skin temperature signal T(k) is obtained by the CPU 45 of FIG. 8 through linear regression over $N_T$ past samples, according to the following equation (7):

$$mT(k) = \frac{N_T \sum jT(k-j-N_T) - \sum j \sum T(k-j-N_T)}{N_T \sum j^2 - \sum j \sum j} \qquad (7)$$

where $k >= N_T$, and where the summations are calculated over $1 <= j <= N_T$.

In a working model of the preferred embodiment, $N_T=30$. Thereby, a moving slope estimate mT(k) is obtained every 30 seconds nominally, and represents the trend of the skin temperature observed over the immediately preceding 15 minutes. As $N_T$ is a predefined constant in a working model of the preferred embodiment, equation (7) may be advantageously simplified to:

$$mT(k) = \frac{N_T \sum jT(k-j) - U_N \sum T(k-j)}{D_N} \qquad (8)$$

where the constants $U_N$ and $D_N$ are obtained from the summations of index j and $j^2$ appearing in equation (7).

For every MT samples of skin temperature signal TS(n), sample mean T(k) as given by equation (6) and slope estimate $mT(k>=N_T)$ as given by equation (8) are calculated by the CPU 45 of FIG. 8, requiring in total $(2N_T+M_T)$ 16-bit summations and $(N_T+5)$ 16×16 bit fixed-point multiplications. Given the interrupt period of WDT 38 is nominally 2.3 seconds, such calculations are manageable in the interval separating measurement of TS(n) and GS(n), but are challenging for the limited data processing speed of the microcontroller 30 in a working model of the preferred embodiment, given that subsequent calculations must also be executed.

Therefore, an alternative embodiment may obtain a slope estimate derived from Taylor series expansion of the skin temperature T(k) as observed only at the current, $N_T/2$, and $N_T$ past samples:

$$mT(k)=(-3T(k)+4T(k-N_T/2)-T(k-N_T))/N_T \qquad (9)$$

where again $k>=N_T$.

The slope estimate given by equation (9) therefore considers terms up to and including the second derivative in the Taylor series expansion. Persons skilled in the art will recognize the computational advantages of the slope estimate of equation (9) are obtained at the expense of estimation accuracy, or equivalently, suppression of noise that may be present in signal T(k) despite smoothing achieved by the sample mean equation (6).

After calculating equation (8) or equation (9), the CPU 45 of FIG. 8 compares the slope estimate mT(k) to a slope threshold which is representative of a hypoglycemic drop in skin temperature observed over a predetermined interval, for example, 15 minutes as predefined by $N_T=30$ above. The CPU 45 will produce an alarm indication according to section 2.1.1 given the following condition:

$$mT\mathrm{min}<mT(k)<mTH(k) \qquad (10)$$

where slope thresholds mTmin and mTH(k) are both less than zero.

Therefore, if the skin temperature as represented by T(k) is rising based on previous observation of NT samples (mT(k)>0), or if skin temperature is gradually falling at a rate not exceeding mTH(k), the CPU 45 does not produce an alarm. Thereby, this method accommodates the warm-up from room temperature which the module 14 experiences after initial application of the strap 11 to a limb per FIG. 1, as well as slow declines in the basal skin temperature which may occur as a result of autonomic thermoregulation of body core temperature.

The stress reaction to hypoglycemia induces a more rapid decline in skin temperature as cutaneous vasoconstriction arrests the skin blood flow, invoking the alarm indication via the CPU 45 when the condition given by (10) is satisfied. In a working model of the preferred embodiment, slope threshold mTH(k) typically ranges from $-0.04°$ C./min to $-0.13°$ C./min, depending on heat loss corrections applied to mTH (k) at sample instant k, as will be described later.

Trend analysis of skin temperature T(k) as described is also useful for rejecting artifacts, such artifacts arising from transient environmental disturbances such as air drafts, or from body movement. This is particularly important if the simplified slope estimate given by (9) is utilized as this is more sensitive to temperature disturbance than linear regression analysis incorporating all $N_T$ samples. The lower bound mTmin of (10) thus defines a maximum rate of skin temperature decline which can be achieved physiologically, and in a working model of the preferred embodiment, mTmin is set to a predetermined value of $-0.3°$ C./min. According to the conditions given by (10), slope estimates less than mTmin are rejected as artifacts and the CPU 45 of FIG. 8 will not produce an alarm in this case.

Because of radiative and evaporative heat losses from the epidermal surface, it is necessary to compensate threshold mTH(k) for these effects to prevent false alarms. To achieve this, slope threshold mTH(k) is calculated by the CPU 45 at sample instants $k>=N_T$ according to:

$$mTH(k)=mT_o-f[GS(k)]-g[T(k)] \quad (11)$$

where $mT_o$ is a predetermined constant slope of approximately $-0.05°$ C./min in a working model of the preferred embodiment. As given by equation (11), g[T(k)] is a positive increasing function of the skin temperature signal T(k), and f[GS(k)] is a positive increasing function of the conductivity signal GS(n) observed at sample instant n=k, GS(k) being directly representative of the level of perspiration.

Perspiration causes a thermodynamic decline in skin temperature through evaporation. According to (11), function f[GS(k)] decreases slope threshold mTH(k) as perspiration increases, thus reducing sensitivity to downward trend in the skin temperature and thereby preventing a false alarm from the evaporative effect. Perspiration may arise through normal autonomic regulation of core body temperature, or as an adrenergic symptom of hypoglycemia. Therefore, a tradeoff exists in choice of f[GS(k)] in balancing rejection of false alarms due to normal perspiration, and detection of valid hypoglycemic symptoms.

However, the invention also monitors perspiration as an indicator of hypoglycemic symptoms and will alarm in the presence of perspiration if specific conditions are met. For example, the CPU 45 of FIG. 8 may produce an alarm indication if the conductance signal GS(n) as calculated from equation (4) exceeds a predetermined threshold, for example 5 micro-mho, this threshold being representative of a hypoglycemic level of perspiration.

Alternatively, more sophisticated processing of conductance signal GS(n) may be applied as will be described later. Monitoring of perspiration also provides backup means of detecting hypoglycemic symptoms during the first 15 minutes of operation following activation of the module 14, in which initial temperature data T(k) are being collected to obtain the first slope estimate $mT(k=N_T)$.

Given alarm means responsive to perspiration as described, the correction f[GS(k)] is included in the present invention primarily as a means of increasing sensitivity to temperature drop when perspiration is low (i.e. f[GS(k)]=0), this being a mechanism for improving detection of hypoglycemic symptoms in those individuals exhibiting blunted adrenergic response due to, for example, diabetic neuropathy or hypoglycemia unawareness. As a secondary feature, the evaporative heat loss correction is seen as a means of validating a temperature drop as being a definite adrenergic symptom (f[GS(k)] non-zero) as opposed to a temperature artifact due to changing environmental conditions. In this way, function f[GS(k)] aids in reducing false alarms.

In the working model of the preferred embodiment, a simple model of the evaporative heat loss is implemented as:

$$f[GS(k)]=Q_{EV}*GS(k) \quad (12)$$

where constant $Q_{EV}$ is predetermined such that the maximum correction applied to threshold mTH(k) is approximately $-0.03°$ C./min, this occurring at the maximum measurable perspiration level which results in parameter bR shown in equation (4) being equal to 15. Persons skilled in the art will recognize the limitations of the evaporative heat loss model given by (12), this being chosen in part to accommodate the computational limitations of the microcontroller 30 shown in FIG. 8.

Any linear or non-linear compensating function f[GS(k)], such as discrete corrections f[GS(k)] corresponding to discrete threshold levels of GS(k), may be implemented as derived from process modelling or experimental observations. In a working model of the preferred embodiment, discrete corrections f[GS(k)] are in effect applied to threshold mTH(k) as the conductance signal GS(n) takes only one of 16 possible values defined by the range of bR. Function f[GS(k)] may therefore be implemented in the ROM 46 of FIG. 8 as a lookup table of discrete corrections, the table being indexed by bR corresponding to GS(k).

Positive increasing function g[T(k)] of equation (11) compensates threshold mTH(k) for radiative heat loss from the skin to the ambient environment, which is at a lower temperature than the skin. As absolute skin temperature increases, radiative loss increases and so a greater rate of decline may be observed at higher skin temperature when hypoglycemia is present. In other words, the epidermal surface follows Newton's law of cooling when hypoglycemic vasoconstriction arrests the cutaneous blood flow, removing the heat source which would otherwise maintain the temperature.

The slope threshold mTH(k) is thus decreased by function g[T(k)] to make classification of a hypoglycemic temperature drop more stringent at higher skin temperature. Conversely, at lower absolute skin temperatures, a fall in skin temperature may occur more slowly given a hypoglycemic state.

Therefore, slope threshold mTH(k) is increased by function g[T(k)] to make hypoglycemic symptom detection less stringent. Effects according to Newton's law of cooling are modelled in the present invention by the following compensating function:

$$g[T(k)]=0, \; T(k)<=TA \quad (13a)$$

$$g[T(k)]=mRAD*(T(k)-TA), \; T(k)>TA \quad (13b)$$

where TA is a predetermined constant representative of a nominal ambient temperature, for example 25° C., and where mRAD is chosen such that the correction applied to mTH(k) is approximately −0.05° C./min at a skin temperature of 37° C. in a working model of the preferred embodiment.

Persons skilled in the art will recognize the limitations of the rudimentary heat loss model given by (13a) and (13b), this being chosen in part to accommodate the computational limitations of the microcontroller 30 shown in FIG. 8. Any linear or non-linear compensating function g[T(k)], such as discrete corrections g[T(k)] corresponding to discrete threshold levels of T(k), may be implemented as derived from process modelling or experimental observations.

In summary of the foregoing and with reference to FIGS. 1 and 8, apparatus for detecting symptoms of hypoglycemia comprises the electronics module 14 in wrist the strap 11 and includes means for producing temperature signal TS(n) representative of the skin temperature, such means being the thermistor 22, resistors RD and RC, capacitor C1, the VREF 61, the WDT 48, and the CPU 45 executing a subroutine of instructions in the ROM 46 according to the method described in section 2.1.3.

Conductance sensing means produces conductance signal GS(n) representative of a level of perspiration, such means being the electrodes 19 and 20, resistor RB, the VREF 61 and the CPU 45 executing a subroutine according to the method described in section 2.1.4.

Trending means the CPU 45 responds to temperature signal TS(n) and produces a slope estimate mT(k) as given by equations (6) and (8) or (9), mT(k) representing the rate of change of the skin temperature over a predetermined interval, said interval being 15 minutes in a working model of the preferred embodiment. Threshold means the CPU 45 responds to conductance signal GS(n) and temperature signal TS(n) at sample instant n=k, and produces a slope threshold mTH(k) representative of a hypoglycemic decline in skin temperature as observed over the predetermined interval.

The CPU 45 will produce an indication of the presence of hypoglycemic symptoms when the slope estimate mT(k) falls below the slope threshold mTH(k). However, the CPU 45 will not produce an alarm if the slope estimate mT(k) falls below an artifact rejection threshold mTmin, mTmin representing a rate of change of the skin temperature not indicative of hypoglycemic symptoms. According to equations (11) and (12), threshold means the CPU 45 decreases slope threshold mTH(k) as the level of perspiration increases, and the CPU 45 increases slope threshold mTH(k) as the level of perspiration decreases.

According to equations (11), (13a) and (13b), threshold means the CPU 45 decreases slope threshold mTH(k) as the skin temperature increases, and increases slope threshold mTH(k) as the skin temperature decreases. The CPU 45 will also produce an alarm indication when the level of perspiration rises above a predetermined threshold, such as the level at which GS(n) exceeds 5 micro-mho, this representing a hypoglycemic level of perspiration.

2.2.2 Detection of Hypoglycemic Perspiration Symptoms

A limitation of the detection scheme discussed in section 2.2.1 is the method described for detecting perspiration symptoms through comparison of conductance GS(n) to a fixed, predetermined threshold. Improved detection of perspiration due to hypoglycemia may be obtained by considering the principle characteristics of such perspiration as represented in the skin conductance.

In very general terms, and considering that geometry and spacing of the electrodes 19 and 20 appearing in FIG. 7 has some influence, very dry skin has a measured conductance in the range of 0.5 to 1 micro-mho, whereas a high level of perspiration may result in a conductance in the 10 to 20 micro-mho range. In practise, therefore, the wide dynamic range of the conductance signal observed with perspiration simplifies the detection problem to some extent, which is why some prior art has proven effective with specific individuals in a limited number of situations. For example, the Sleep Sentry™ (Teledyne Avionics, Charlottesville Va.) utilizes a fixed conductance threshold of 5.3 micro-mho to declare an alarm based on hypoglycemic perspiration.

The present invention improves on prior art by using an adaptive detection threshold which corrects for basal perspiration, and for perspiration which arises due to normal physiological reaction to increased core body temperature. Basal perspiration must be accounted for since free evaporation of perspiration is somewhat limited by obstruction of the skin from the module 14. Therefore, a background level of perspiration develops under the module 14 after a few minutes of application to the limb, for example as shown in FIG. 1, this basal perspiration generally being in the range of 2 to 4 micro-mho, depending on the individual being monitored.

To obtain a value representative of the basal perspiration level following initial activation of the module 14, the CPU 45 of FIG. 8 monitors skin temperature signal T(k) as given by equation (6), and thereby determines a sample instant $k_O$ at which the following condition is satisfied:

$$T(k_O)-T(k_O-1)<mWU \tag{14}$$

where mWU>0 is a predetermined slope threshold.

By calculating a first-order backward difference of T(k), the CPU 45 observes the thermal warm-up of the module 14, which is seen in the case where the module 14 is activated immediately after being applied to the limb as shown in FIG. 1. During the warm-up, temperature of the module 14 increases and the first-order backward difference of T(k) remains greater than mWU. Once the temperature of the module 14 has equilibrated with the skin temperature, equation (14) is satisfied, and conditions at the epidermal surface are thus considered stable enough to obtain a basal conductance reference representative of the basal level of perspiration.

The CPU 45 estimates a basal conductance reference BGS by calculating a sample mean of the conductance signal GS(n) as follows:

$$BGS = \sum_{j=N_o}^{j=N_o+M_G-1} GS(n)/M_G \tag{15}$$

where $N_O=k_O*M_T$, and where $M_G$ is predetermined to correspond to a 3-minute observation interval, as obtained by the CPU 45 from the calibration factor for WTD 38 of FIG. 8, according to the method described in section 2.1.2.

Persons skilled in the art will recognize the sample mean of (15) as a rudimentary form of signal estimation; other forms of basal estimation are possible by means of autoregressive low-pass filtering and similar techniques, however, the sample mean of (15) is appropriate given the limited data processing ability of the microcontroller 30 of FIG. 8, and the relatively static nature of the signal being estimated.

Once basal conductance reference BGS has been determined, the CPU 45 obtains a conductance threshold GH(n) according to:

$$GH(n)=BGS+dG+h[TS(n)] \tag{16}$$

where dG is a predetermined conductance corresponding to a hypoglycemic increase in perspiration above the basal reference level, and where h[TS(n)] is a positive increasing function of the skin temperature signal TS(n). In a working model of the preferred embodiment, conductance dG is approximately +7 micro-mho.

According to equation (16), function h[TS(n)] is added to the basal conductance reference BGS to compensate for increased perspiration which is concurrently observed with cutaneous vasodilation, or an increase in skin blood flow. Cutaneous vasodilation is a normal autonomic response to elevated core body temperature. Increased perspiration is also a normal autonomic response to increased core temperature, and thus the correction introduced by h[TS(n)] is seen as a mechanism for preventing false alarms from a non-hypoglycemic reaction.

Conversely, if the skin is colder, the correction introduced by h[TS(n)] is ideally zero, and so perspiration detected under such conditions would be considered a more valid indicator of hypoglycemia. This suggests a potential model for the skin temperature correction is:

$$h[TS(n)]=0, \; TS(n)<=TP \tag{17a}$$

$$h[TS(n)]=K_p*(TS(n)-TP), \; TS(n)>TP \tag{17b}$$

where TP is a skin temperature corresponding to the onset of normal perspiration due to, for example, environmental conditions, and where $K_P$ is chosen such that the correction applied at 37° C. is approximately +3 micro-mho in a working model of the preferred embodiment.

Persons skilled in the art will recognize that any linear or non-linear compensating function h[TS(n)], such as discrete corrections h[TS(n)] corresponding to discrete threshold levels of TS(n), may be implemented as derived from process modelling or experimental observations.

As the final step in detecting a hypoglycemic symptom, the CPU 45 of FIG. 8 compares the conductance signal GS(n) to the compensated conductance threshold GH(n), and will produce an alarm indication according to section 2.1.1 given the following condition:

$$GS(n)>GH(n) \tag{18}$$

As described previously, individual samples TS(n) or GS(n) may be corrupted by environmental or motion artifacts. Therefore, the comparison as given by (18) is sensitive to such artifacts and so false alarms may result. One way to remove such artifacts is to smooth GS(n) prior to the comparison (18) with a moving average, for example:

$$AG(n) = \sum_{j=0}^{j=N_C-1} GS(n-j)/N_c \tag{19}$$

with smoothed skin conductance AG(n) thereby replacing GS(n) in (18) above.

Alternatively, since GS(n) is compared to the discrete threshold GH(n), a simpler approach which achieves an equivalent result is to require at least Nc consecutive samples of GS(n) to remain above threshold GH(n) before the CPU 45 produces an alarm indication. This is the approach taken in a working model of the preferred embodiment due to the computational simplicity.

By requiring $N_C$ consecutive samples of GS(n) to be greater than threshold GH(n), the probability of error is reduced as a function of Nc. In a working model of the preferred embodiment, the data interval of GS(n) is 4.6 seconds and $N_C$=4, so that the worst case alarm lag in the event of hypoglycemia under noiseless conditions is approximately 18.4 seconds, a relatively short interval compared to the physiological response times under consideration.

It should be noted that basal reference level BGS is initialized by the CPU 45 with a zero value when the module 14 is initially activated by the user. However, the test condition given by equation (18) is evaluated by the CPU 45 at each sample instant n. An alarm will therefore be produced if a high level of perspiration is preexisting at the time of application of the module 14 to a limb. As will be described in section 2.3, the invention provides means for disabling the perspiration alarm in this case. The user may also employ this feature to verify basic function of the module 14 immediately upon activation, for example, by means of a wetted finger pressed across the electrodes 19 and 20 of FIG. 7.

The invention also monitors skin temperature as an indicator of hypoglycemic symptoms and will alarm if the skin temperature decreases. Thus, the CPU 45 of FIG. 8 may produce an alarm indication if the skin temperature signal TS(n) falls below a predetermined threshold, for example a threshold equal to TS(0)−2° C., where TS(0) is the first skin temperature obtained immediately after device activation. Alternatively, more sophisticated processing of the skin temperature signal TS(n) may be applied along the lines discussed earlier, in which an estimate of the rate of change of signal TS(n) is compared to a compensated slope threshold mTH(k) as given by (11), and in which an alarm indication is produced if the condition given by (10) is satisfied.

In summary of the foregoing and with reference to FIG. 8, the apparatus 10 for detecting symptoms of hypoglycemia may include means for producing temperature signal TS(n) representative of the skin temperature according to the method described in section 2.1.3. Conductance sensing means produces conductance signal GS(n) representative of a level of perspiration according to the method described in section 2.1.4. Signal estimation means the CPU 45 responds to skin temperature signal TS(n) and conductance signal GS(n), and produces a basal conductance reference BGS as given by equations (14) and (15), BGS representing a basal level of perspiration.

According to equation (16), threshold means the CPU 45 responds to basal conductance reference BGS and to skin temperature signal TS(n), and produces a conductance threshold GH(n) representative of a hypoglycemic level of perspiration. The CPU 45 will produce an indication of the presence of hypoglycemic symptoms when the skin conductance signal GS(n) rises above the conductance threshold GH(n). To reduce false alarms, the CPU 45 does not produce an alarm indication unless the conductance signal GS(n) remains above conductance threshold GH(n) for a predetermined length of time, this being $N_C$=4 samples of GS(n) corresponding to approximately 18.4 seconds in a working model of the preferred embodiment.

According to equations (14) and (15), the CPU 45 produces the basal conductance reference BGS by obtaining the mean of the conductance signal GS(n) over a predetermined averaging interval MG, MG corresponding to a duration of 3 minutes in a working model of the preferred embodiment. According to equations (17a) and (17b), threshold means the CPU 45 increases conductance threshold GH(n) as skin temperature increases, and decreases conductance threshold GH(n) as skin temperature decreases. The CPU 45 will also produce an alarm indication when the skin temperature conveyed by TS(n) falls below a predetermined threshold representative of a hypoglycemic skin temperature.

2.3 Operating Modes

Basic system functions described in section 2.1 provide means for producing a temperature signal TS(n) representative of a skin temperature, and for producing a conductance signal GS(n) representative of a level of perspiration, GS(n) and TS(n) being obtained approximately once every 4.6 seconds in a working model of the preferred embodiment.

The CPU 45 calculates signal GS(n) according to equation (4) on an odd-numbered interrupt from WDT 38 of FIG. 8, and signal TS(n) on the subsequent even-numbered interrupt, single examples of odd- and even-numbered interrupts being respectively represented by pulses 70 and 71 of the signal 49 in FIG. 9. Following determination of TS(n) on each even-numbered interrupt, the CPU 45 further processes TS(n) and GS(n) according to methods and equations disclosed in section 2.2. If conditions specified in section 2.2 are met, the CPU 45 produces an audible alarm by means of the speaker 27, and according to section 2.1.1, the CPU 45 will continue to produce the alarm until the module 14 is deactivated by the user.

Signal processing algorithms described in section 2.2 are embodied in the invention as subroutines of instructions in the ROM 46 of FIG. 8. In the preferred embodiment, these signal processing subroutines are combined in various ways to comprise a plurality of operating modes of the invention. As described below, the invention incorporates selector means for selecting one of the operating modes from the plurality, thereby allowing the invention to be adapted to the particular autonomic physiology of each diabetic individual.

The first operating mode of the invention is intended to provide a simulation of the prototype version of the Sleep Sentry™ monitor manufactured by Teledyne Avionics of Charlottesville Va., this prototype monitor having been clinically evaluated in studies by Hansen et al. (Diabetes Care, 6:597–600 (1983)) and Clarke et al. (Diabetes Care, 11:630–35 (1988)). The first operating mode is included in the preferred embodiment primarily for comparison with the other operating modes in clinical studies. When instructed to execute the first operating mode, the CPU 45 periodically obtains signals TS(n) and GS(n) as described previously, and will produce an alarm if either of the two following conditions is encountered:

$$TS(n) < TS(0) - 2° C., n > 0 \quad (20a)$$

$$GS(n) > 5.3 \text{ micro-mho} \quad (20b)$$

where TS(0) is the skin temperature signal obtained immediately after activation of the module 14.

In comparison to signal processing algorithms previously described, equation (20a) indicates that no trend analysis is applied to the skin temperature, and as such any effect which causes a drop of 2° C. from the initial temperature TS(0), regardless of the time interval over which the drop is measured, will produce the alarm. No corrections are applied to the threshold represented by the right-hand side of (20a) to accommodate heat loss caused by evaporation of perspiration or radiation.

Equation (20b) shows the perspiration as represented by conductance GS(n) is not corrected for the basal perspiration, or for perspiration which is seen with increasing skin temperature. Nevertheless, these simple detection rules have proven effective in specific and limited circumstances, and as discussed above, the algorithm represented by equations (20a) and (20b) has been included in the preferred embodiment for purposes of clinically comparing performance with the more sophisticated signal processing methods disclosed in section 2.2.

When instructed to execute the second operating mode, the CPU 45 periodically obtains signals TS(n) and GS(n), obtains the slope estimate mT(k) according to equations (6) and (8) or (9) of section 2.2, calculates the compensated slope threshold mTH(k) as given by equations (11) through (13b), and produces an alarm indication if mT(k) lies within the bounds defined by equation (10). When running the second operating mode, the CPU 45 will also produce an alarm indication if condition (20b) above is satisfied by the perspiration level.

The third operating mode of the invention is similar to the second operating mode, except that condition (20b) is not tested by the CPU 45 and so the means for producing a perspiration alarm is disabled. This mode is intended to accommodate individuals who freely perspire in reaction to elevated environmental temperature, this potentially resulting in false alarms from the test of (20b). Thereby, detection of hypoglycemic symptoms in the third operating mode is obtained solely from a decline in temperature signal T(k) faster than slope threshold mTH(k), mTH(k) being compensated for perspiration by function f[GS(k)]. As described in section 2.2, function f[GS(k)] decreases the slope threshold to correct for temperature drops caused by the significant evaporative heat loss in this case.

When instructed to run the fourth operating mode, the CPU 45 periodically obtains signals TS(n) and GS(n), obtains a compensated conductance threshold GH(n) according to equations (14), (15) and (16) of section 2.2, and produces an alarm indication per equation (18) if GS(n) remains above threshold GH(n) for $N_C = 4$ consecutive samples as described previously. When running the fourth operating mode, the CPU 45 will also produce an alarm indication if condition (20a) above is satisfied by the skin temperature.

The fifth operating mode of the invention is similar to the fourth operating mode, except that condition (20a) is not tested by the CPU 45 and so the means for producing a temperature alarm is disabled. This mode is intended to accommodate situations where environmental conditions may not be well-controlled, such as when the diabetic individual is operating a motor vehicle.

Although the invention is primarily intended for detecting symptoms of nocturnal hypoglycemia, the proposed application is not unreasonable when considering the severe consequences of hypoglycemia leading to nueroglycopenic symptoms while driving. However, the unstable environment of a motor vehicle could foreseeably induce false temperature alarms which could be distracting. Thereby, detection of hypoglycemic symptoms in the fifth operating mode is obtained solely from conductance GS(n) exceeding the conductance threshold GH(n), threshold GH(n) being compensated for skin temperature by function h[TS(n)].

As described in section 2.2, function h[TS(n)] corrects threshold GH(n) downward with decreasing skin temperature, so that in the event a hypoglycemic drop in skin temperature is experienced, threshold GH(n) is decreased and thus sensitivity to a hypoglycemic perspiration is increased. Advantageously, responsiveness to the hypoglycemic temperature condition is not completely eliminated by the fifth operating mode.

When instructed to execute the sixth operating mode, the CPU 45 periodically obtains signals TS(n) and GS(n), and according to methods disclosed in section 2.2, the CPU 45 obtains the slope estimate mT(k), calculates the compensated slope threshold mTH(k), and produces an alarm indication if mT(k) lies within the bounds defined by equation (10). The CPU 45 also obtains a compensated conductance threshold GH(n) according to equation (16), and produces an alarm indication if GS(n) remains above threshold GH(n) for $N_C$=4 consecutive samples as described previously in section 2.2.

Additional operating modes are also provided, these being the sixth operating mode above with alternate values of $M_T$, $N_T$, $mT_O$, $M_G$, dG and $N_C$ as appearing in equations (6), (8), (11), (15), (16) and (18) of section 2.2 respectively. For example, modes which provide increased or decreased values of MT or NT compared to the examples provided in section 2.2 respectively introduce increased or decreased smoothing of the estimated slope, as may be appropriate to the monitoring situation or the physiology of certain individuals.

Modes which provide increased or decreased values of $mT_o$ respectively provide an increase or decrease in the basic, uncompensated sensitivity of the invention to temperature decline. As such, there is some interaction between parameters $M_T$, $N_T$ and $mT_O$, and thus an operating mode which provides an alternate value for one parameter also provides an alternate value for at least one of the other two.

Modes which provide increased or decreased dG respectively provide a decrease or increase in the basic, uncompensated sensitivity of the invention to perspiration. Modes which provide increased or decreased values of $N_C$ compared to the example provided in section 2.2 respectively produce increased or decreased certainty in detection of the perspiration symptom, which is traded off against decreased or increased responsiveness of the invention to the alarm condition.

Further operating modes function according to the sixth operating mode, except that threshold-compensating functions disclosed, such as f[GS(k)], g[T(k)], or h[TS(n)] respectively appearing in section 2.2, are disabled such that a zero functional result is obtained regardless of the value of the respective independent variable GS(k), T(k) or TS(n). Such operating modes are provided given the generalized and simplified nature of the physical models described by f[GS(k)], g[T(k)], and h[TS(n)] respectively, which may not be well-suited to a particular individual or monitoring situation, and which may therefore degrade rather than improve performance in the manner described.

In a working model of the preferred embodiment, an operating mode is selected from the plurality of operating modes by means of the serial communications interface described in section 2.1.6. To set the operating mode of the invention, the module 14 of FIG. 7 is removed from the strap 11 according to the procedure given in section 1, and an external device such as a personal computer is connected to the exposed the interface connector 29.

Referring to FIG. 8, and according to the method described in section 2.1.6, data received from the personal computer by means of the RXD signal 59 causes the CPU 45 to program the non-volatile memory EEPM 68 with a byte representative of the selected operating mode of the invention, the operating mode being conveyed by the content of the data from the personal computer. Such data, for example, may simply comprise two ASCII characters, the first character received by the CPU 45 indicating the character immediately following is to be interpreted as the desired operating mode.

When the module 14 is activated by the user, the operating mode is retrieved from the EEPM 68 by the CPU 45 which then proceeds to execute the selected operating mode as described above. Persons skilled in the art will recognize that any means capable of serial data transmission, such as a small microcontroller, digital circuit, or application-specific IC, may be used in place of the personal computer to set the operating mode as selected by, for example, a set of pushbutton switches.

Novel apparatus has been disclosed for detecting symptoms of hypoglycemia with improved ability to distinguish such symptoms from non-symptomatic physiological variations. It is evident that given the preceding description of the preferred embodiment, persons skilled in the art may now make numerous uses of, modifications of, and departures from the preferred embodiment of the invention without departing from the principles of the invention.

For example, persons skilled in the art may be able to provide alternate sensing means, such as a pre-calibrated semiconductor temperature sensor with integrated analog-to-digital converter, for conveniently producing data directly proportional to the skin temperature.

Rather than provide alternate temperature sensing means, persons skilled in the art may recognize the inverse but direct relationship between resistance RT of the thermistor 22 and skin temperature, and through application of the signal processing methods disclosed in section 2.2, be able to derive a slope estimate mR(k) for a thermistor resistance signal RT(n), as well as a slope threshold mRH(k) which is dependent on a function g[RT(k)]. This would obviate the additional step of conversion to temperature TS(n) by means of lookup methods such as Table I given in section 2.1.3.

Methods disclosed for producing and processing temperature signal TS(n) have been provided herein to clearly illustrate the principles of the invention in light of the physiological variables observed, and an alternate working model of the preferred embodiment which obtains signals mR(k) and mRH(k) as described above may be implemented within the scope of the appended claims.

Persons skilled in the art will be aware of many methods applicable to estimation of a signal or data trend. Linear regression as a means of determining signal trend and moving average as a means of smoothing or estimation have been chosen to illustrate principles of the invention as such methods are well understood by persons skilled in the art.

Superior methods of signal and trend estimation, such as autoregressive analysis, exist but are beyond the data processing capabilities of the computing platform chosen for a working model of the preferred embodiment. As computing devices improve, it is foreseeable that such improved estimation methods could be implemented to obtain and utilize the trend information in the manner disclosed, by means of a low-cost, low-power computing device which may be applied, for example, at the wrist.

Just as improved trending means may be implemented, so may more sophisticated models of evaporative and radiative heat loss be developed from computer simulation studies or experimental observations, such models being used to compensate the detection thresholds according to the methods of section 2.2. For example, an improved model of heat loss due to evaporation may include the rate of change of the perspiration, as well as or in place of the level of perspiration represented by the skin conductance as shown in equation (12).

Examples provided for constants and predetermined thresholds utilized in the working model of the preferred embodiment, for example $M_T$, $N_T$, $mT_O$, mTmin, $Q_{EV}$, mRAD, TA, mWU, $M_G$, dG, $K_P$, TP and $N_C$ appearing in the description of section 2.2, are for purposes of illustration only and should not be construed as limiting the invention. According to section 2.3, operating modes of the invention may modify the value of the example constants and thresholds as disclosed, to achieve alternate objects given the monitoring situation or the particular physiology of the individual being monitored.

In light of the foregoing and other examples, the invention is therefore not limited to the details given herein, but may be modified within the scope of the appended claims.

We claim:

1. A system for detecting symptoms of hypoglycemia in a diabetic individual, comprising:
   a temperature sensing system for producing a temperature signal representative of a skin temperature of the diabetic individual;
   a conductance sensing system for producing a conductance signal representative of a level of perspiration of the diabetic individual;
   a trending system responsive to the temperature signal for producing a slope estimate representative of a rate of change of the skin temperature over a predetermined interval;
   a threshold system responsive to the conductance signal and to the temperature signal for producing a slope threshold representative of a hypoglycemic decline in skin temperature observed over the predetermined interval; and
   an alarm system responsive to the slope estimate and to the slope threshold for producing an indication of the presence of hypoglycemic symptoms.

2. A system as defined in claim 1, wherein the alarm system produces the indication when the slope estimate falls below the slope threshold.

3. A system as defined in claim 2, wherein the alarm means does not produce the indication when the slope estimate falls below an artifact rejection threshold, the artifact rejection threshold representing a rate of change of the skin temperature not indicative of hypoglycemic symptoms.

4. A system as defined in claim 3, wherein the artifact rejection threshold is less than the slope threshold.

5. A system as defined in claim 1, wherein the trending system produces the slope estimate through a linear regression analysis.

6. A system as defined in claim 1, wherein the threshold system decreases the slope threshold when the level of perspiration increases, and wherein the threshold system increases the slope threshold when the level of perspiration decreases.

7. A system as defined in claim 1, wherein the threshold system decreases the slope threshold when the skin temperature increases, and wherein the threshold means increases the slope threshold when the skin temperature decreases.

8. A system as defined in claim 1 wherein the alarm system produces an indication of the presence of hypoglycemic symptoms when the level of perspiration rises above a predetermined threshold representative of a hypoglycemic level of perspiration.

9. A system as defined in claim 8 wherein the alarm system produces an indication of a depleted battery when a battery potential falls below a predetermined battery alarm threshold.

10. A system as defined in claim 9 further comprising a strap formed of hypoallergenic and conformable elastomer and defining a stretchable recess, a hook fabric strip, and a loop fabric strip.

11. A system as defined in claim 9 further comprising an elastomeric cup defining a stretchable recess and a spring clip member.

12. A system for detecting symptoms of hypoglycemia in a diabetic individual, comprising:
    a temperature sensing system for producing a temperature signal representative of a skin temperature of the diabetic individual;
    a conductance sensing system for producing a conductance signal representative of a level of perspiration of the diabetic individual;
    a signal estimation system responsive to the temperature signal and to the conductance signal for producing a basal conductance reference representative of a basal level of perspiration;
    a threshold system responsive to the basal conductance reference and to the skin temperature signal for producing a conductance threshold representative of a hypoglycemic level of perspiration; and
    an alarm system responsive to the conductance signal and to the conductance threshold for producing an indication of the presence of hypoglycemic symptoms.

13. A system as defined in claim 12, wherein the alarm system produces the indication when the conductance signal rises above the conductance threshold.

14. A system as defined in claim 13, wherein the alarm system produces the indication when the conductance signal rises above the conductance threshold for a predetermined length of time.

15. A system as defined in claim 12, wherein the signal estimation system produces the basal conductance reference by obtaining the mean of the conductance signal over a predetermined averaging interval.

16. A system as defined in claim 15, wherein the signal estimation system produces the basal conductance reference after a rate of change of the skin temperature signal falls below a predetermined slope threshold.

17. A system as defined in claim 12, wherein the threshold system increases the conductance threshold when the skin temperature increases, and wherein the threshold system decreases the conductance threshold when the skin temperature decreases.

18. A system as defined in claim 12 wherein the alarm system produces an indication of the presence of hypoglycemic symptoms when the skin temperature falls below a predetermined temperature threshold representative of a hypoglycemic skin temperature.

19. A system for detecting symptoms of hypoglycemia in a diabetic individual, comprising:
    a temperature sensing system for producing a temperature signal representative of a skin temperature of the diabetic individual;
    a conductance sensing system for producing a conductance signal representative of a level of perspiration of the diabetic individual;
    a trending system responsive to the temperature signal for producing a slope estimate representative of a rate of change of the skin temperature over a predetermined interval;
    a temperature threshold system responsive to the conductance signal and to the temperature signal for producing a slope threshold representative of a hypoglycemic decline in skin temperature observed over the predetermined interval;

a temperature alarm system responsive to the slope estimate and to the slope threshold for producing an indication of the presence of hypoglycemic symptoms;

a signal estimation system responsive to the temperature signal and to the conductance signal for producing a basal conductance reference representative of a basal level of perspiration;

a conductance threshold system responsive to the basal conductance reference and to the temperature signal for producing a conductance threshold representative of a hypoglycemic level of perspiration;

a conductance alarm system responsive to the conductance signal and to the conductance threshold for producing an indication of the presence of hypoglycemic symptoms; and a selector system for selecting an operating mode from a plurality of operating modes.

20. A system as defined in claim 19, wherein one of the operating modes disables the conductance alarm means.

21. A system as defined in claim 19, wherein one of the operating modes disables the temperature alarm means.

22. A system as defined in claim 19, wherein the one of the operating modes prevents the temperature threshold means from responding to the conductance signal.

23. A system as defined in claim 19, wherein the one of the operating modes prevents the temperature threshold means from responding to the temperature signal.

24. A system as defined in claim 19, wherein one of the operating modes prevents the conductance threshold means from responding to the temperature signal.

25. A method of detecting symptoms of hypoglycemia in a diabetic individual, comprising:

producing a temperature signal representative of a skin temperature of the diabetic individual;

producing a conductance signal representative of a level of perspiration of the diabetic individual;

producing a slope estimate representative of a rate of change of the skin temperature over a predetermined interval in response to the temperature signal;

producing a slope threshold representative of a hypoglycemic decline in skin temperature observed over the predetermined interval in response to the conductance signal and the temperature signal; and producing an indication of the presence of hypoglycemic symptoms in response to the slope estimate and the slope threshold.

26. A method of detecting symptoms of hypoglycemia in a diabetic individual, comprising:

producing a temperature signal representative of a skin temperature of the diabetic individual;

producing a conductance signal representative of a level of perspiration of the diabetic individual;

producing a basal conductance reference representative of a basal level of perspiration in response to the temperature signal and the conductance signal;

producing a conductance threshold representative of a hypoglycemic level of perspiration in response to the basal conductance reference and the skin temperature signal; and producing an indication of the presence of hypoglycemic symptoms in response to the conductance signal and the conductance threshold.

27. A method of detecting symptoms of hypoglycemia in a diabetic individual, comprising:

producing a temperature signal representative of a skin temperature of the diabetic individual;

producing a conductance signal representative of a level of perspiration of the diabetic individual;

producing a slope estimate representative of a rate of change of the skin temperature over a predetermined interval in response to the temperature signal;

producing a slope threshold representative of a hypoglycemic decline in skin temperature observed over the predetermined interval in response to the conductance signal and the temperature signal;

producing an indication of the presence of hypoglycemic symptoms in response to the slope estimate and the slope threshold;

producing a basal conductance reference representative of a basal level of perspiration in response to the temperature signal and the conductance signal;

producing a conductance threshold representative of a hypoglycemic level of perspiration in response to the basal conductance reference and the temperature signal;

producing an indication of the presence of hypoglycemic symptoms in response to the conductance signal and the conductance threshold; and selecting an operating mode from a plurality of operating modes.

* * * * *